US009439976B2

(12) United States Patent
Tung et al.

(10) Patent No.: US 9,439,976 B2
(45) Date of Patent: Sep. 13, 2016

(54) COMPOSITIONS AND METHODS FOR USING CATHEPSIN E CLEAVABLE SUBSTRATES

(71) Applicants: The Methodist Hospital System, Houston, TX (US); Board of Regents, The University of Texas System, Austin, TX (US)

(72) Inventors: Ching-Hsuan Tung, Houston, TX (US); Wael Refat Adb-Elgaliel, Houston, TX (US); Craig D. Logsdon, Houston, TX (US); Zobeida Cruz-Monserrate, Houston, TX (US)

(73) Assignees: THE METHODIST HOSPITAL SYSTEM, Houston, TX (US); BOARD OF REGENTS, THE UNIVERSITY OF TEXAS SYSTEM, Austin, TX (US)

( * ) Notice: Subject to any disclaimer, the term of this patent is extended or adjusted under 35 U.S.C. 154(b) by 0 days.

(21) Appl. No.: 14/179,379

(22) Filed: Feb. 12, 2014

(65) Prior Publication Data

US 2014/0227188 A1    Aug. 14, 2014

Related U.S. Application Data

(60) Provisional application No. 61/764,314, filed on Feb. 13, 2013.

(51) Int. Cl.
| A61K 45/00 | (2006.01) |
| C07K 16/00 | (2006.01) |
| A61K 47/48 | (2006.01) |
| A61K 41/00 | (2006.01) |
| A61K 45/06 | (2006.01) |
| G01N 33/574 | (2006.01) |

(52) U.S. Cl.
CPC ..... *A61K 47/48246* (2013.01); *A61K 41/0057* (2013.01); *A61K 41/0061* (2013.01); *A61K 45/06* (2013.01); *G01N 33/57484* (2013.01)

(58) Field of Classification Search
None
See application file for complete search history.

(56) References Cited

U.S. PATENT DOCUMENTS

| 6,027,892 | A * | 2/2000 | Chang et al. ............ 435/6.11 |
| 6,083,486 | A | 7/2000 | Weissleder et al. |
| 6,592,847 | B1 | 7/2003 | Weissleder et al. |
| 2004/0067927 | A1 | 4/2004 | Boss et al. |
| 2004/0102431 | A1 | 5/2004 | Boss et al. |
| 2006/0275775 | A1 | 12/2006 | Weissleder et al. |
| 2008/0076762 | A1 | 3/2008 | Boss et al. |
| 2009/0311193 | A1 | 12/2009 | Mauro et al. |
| 2010/0124757 | A1 | 5/2010 | Kwon et al. |
| 2012/0225425 | A1 | 9/2012 | Navari et al. |

FOREIGN PATENT DOCUMENTS

| EP | 582477 | 2/1994 |
| JP | 2005117993 | 5/2005 |
| KR | 1020100026477 | 3/2010 |
| WO | 0073437 | 12/2000 |
| WO | 2009111470 | 9/2009 |
| WO | 2010024609 | 3/2010 |

OTHER PUBLICATIONS

Komatsu et. al. International Journal of Peptides, vol. 2012, Article ID 316432, 7 pages.*
Wael R. et. al. (Biochemica et Biophysica Acta, 1800 (2010) 1002-1008.*
Toschi et. al. (Role of Gemcitabine in Cancer Future Oncol. Feb. 2005;1(1):7-17.*
Bourre et. al. (Mol Cancer Ther 2008;7(6). Jun. 2008.*
Abd-Elgaliel et al., "Molecular imaging of Cathepsin E-positive tumors in mice using novel protease-activatable fluorescent probe", Molecular Biosystems, vol. 7, No. 12, Dec. 2011, pp. 3207-3213.
Abd-Elgaliel et al., "Selective Detection of Cathepsin E Proteolytic Activity", Biochimica et Biophysica Acta, vol. 1800, No. 9, Jun. 2010, pp. 1002-1008.
Ai et al., "Biomedical applications of electrostatic layer-by-layer nano-assembly of polymers, enzymes, and nanoparticles", Cell Biochemistry and Biophysics, vol. 39, No. 1, 2003, pp. 23-43.
Amano et al., "Increased expression of cathepsins E and D in reactive microglial cells associated with spongiform degeneration in the brain stem of senescence-accelerated mouse", Experimental Neurology, vol. 136, No. 2, Dec. 1995, pp. 171-182.
AnaSpec, Inc. "FRET Technology The dawn of long wavelength protease FRET assays." 2nd Edition. Published 2008.
Anderson, C. J. et al., "AACR/SNMMI state-of-the-art molecular imaging in cancer biology and therapy: Abstracts," J Nucl Med, 2013, vol. 54, No. Supplement 1, pp. 3A-35.
Arumugam et al., "Epithelial to mesenchymal transition contributes to drug resistance in pancreatic cancer", Cancer Research, vol. 69, No. 14, Jul. 15, 2009, pp. 5820-5828.
Arvizo et al., "Effect of Nanoparticle Surface Charge at the Plasma Membrane and Beyond", Nano Letters, vol. 10, No. 7, Jul. 14, 2010, pp. 2543-2548.
Azuma et al., "Cathepsin E expressed in pancreatic cancer", Advances in Experimental Medicine and Biology, vol. 362, 1995, pp. 363-366.
Azuma et al., "Expression of cathepsin E in pancreas: a possible tumor marker for pancreas, a preliminary report", International Journal of Cancer, vol. 67, No. 4, Aug. 7, 1996, pp. 492-497.
Azuma et al., "Origins of the multiple cathepsin E transcripts observed in human gastric mucosa and gastric adenocarcinoma", Advances in Experimental Medicine and Biology, vol. 306, 1991, pp. 365-368.

(Continued)

*Primary Examiner* — Jeanette Lieb
(74) *Attorney, Agent, or Firm* — Kilpatrick Townsend & Stockton LLP

(57) ABSTRACT

Provided herein are compositions and kits comprising a therapeutic agent linked to a cleavable substrate, wherein the cleavable substrate is capable of being cleaved by cathepsin E. Also provided are methods of treating one or more symptoms of a disease or disorder characterized by expression of cathepsin E in a subject and methods of eliminating a cancer cell characterized by expression of cathepsin E using the provided compositions and kits. Further provided herein are methods of detecting the presence of a cancer cell or detecting a cathepsin E expressing cell using a photosensitizer linked to a cleavable substrate, wherein the cleavable substrate is capable of being cleaved by cathepsin E.

35 Claims, 8 Drawing Sheets

(56) References Cited

OTHER PUBLICATIONS

Baechle et al., "Biotinylated fluorescent peptide substrates for the sensitive and specific determination of cathepsin D activity", Journal of Peptide Science, vol. 11, No. 3, Mar. 2005, pp. 166-174.
Bagalkot et al., "Quantum dot-aptamer conjugates for synchronous cancer imaging, therapy, and sensing of drug delivery based on bi-fluorescence resonance energy transfer", Nano Letters, vol. 7, No. 10, Sep. 14, 2007, pp. 3065-3070.
Bander et al., "Phase I trial of 177lutetium-labeled J591, a monoclonal antibody to prostate-specific membrane antigen, in patients with androgen-independent prostate cancer", Journal of Clinical Oncology, vol. 23, No. 21, Jul. 20, 2005, pp. 4591-4601.
Bardeesy et al., "Both p16(Ink4a) and the p19(Arf)-p53 pathway constrain progression of pancreatic adenocarcinoma in the mouse", Proceedings of the National Academy of Sciences of the USA, vol. 103, No. 15, Apr. 11, 2006, pp. 5947-5952.
Bartoli, M., Bourg, N. et al., "A mouse model for monitoring calpain activity under physiological and pathological conditions," J. Biol. Chem, 2006, vol. 281, No. 51, pp. 39672-39680.
Bausch et al., "Plectin-1 as a novel biomarker for pancreatic cancer", Clinical Cancer Research, vol. 17, No. 2, Jan. 15, 2010, pp. 302-309.
Bennett et al., "Antigen processing for presentation by class II major histocompatibility complex requires cleavage by cathepsin E", European Journal of Immunology, vol. 22, No. 6, Jun. 1992, pp. 1519-1524.
Benveniste et al., "Role of macrophages/microglia in multiple sclerosis and experimental allergic encephalomyelitis", Journal of Molecular Medicine, vol. 75, No. 3, Mar. 1997, pp. 165-173.
Berdowska et al., "Cysteine proteases as disease markers", Clinica Chimica Acta, vol. 342, No. 1-2, Apr. 2004, pp. 41-69.
Berlin, N.I. et al., "The metabolism of delta-aminolaevulic acid. 1. Normal pathways, studied with the aid of 15N," Biochem J, 1956, vol. 64, No. 1, pp. 80-90.
Bervar et al., "Invasiveness of transformed human breast epithelial cell lines is related to cathepsin B and inhibited by cysteine proteinase inhibitors", Biological Chemistry, vol. 384, No. 3, Mar. 2003, pp. 447-455.
Bird et al., "The effects of novel cathepsin E inhibitors on the big endothelin pressor response in conscious rats", Biochemical and Biophysical Research Communications, vol. 182, No. 1, Jan. 15, 1992, pp. 224-231.
Blaveri et al., "Bladder cancer outcome and subtype classification by gene expression", Clinical Cancer Research, vol. 11, No. 11, Jun. 1, 2005, pp. 4044-4055.
Bock et al., "Selection of single-stranded DNA molecules that bind and inhibit human thrombin", Nature, vol. 355, No. 6360, Feb. 6, 1992, pp. 564-566.
Bogdanov et al., "Cellular activation of the self-quenched fluorescent reporter probe in tumor microenvironment", Neoplasia, vol. 4, No. 3, May/Jun. 2002, pp. 228-236.
Bonetta, "RNA-based therapeutics: ready for delivery?", Cell, vol. 136, No. 4, Feb. 20, 2009, pp. 581-584.
Bown SG et al., "Photodynamic therapy for cancer of the pancreas," Gut, 2002, vol. 50, pp. 549-557.
Boyce, "Trial halted after gene shows up in semen", Nature, vol. 414, No. 6865, Dec. 13, 2001, p. 677.
Bremer et al., "In vivo molecular target assessment of matrix metalloproteinase inhibition", Nature Medicine, vol. 7, No. 6, Jun. 2001, pp. 743-748.
Brokx RD et al., "Designing peptide-based scaffolds as drug delivery vehicles," J Control Release, 2002, vol. 78, pp. 115-123.
Brown SB et al., "The present and future role of photodynamic therapy in cancer treatment," Lancet Oncol, 2004, vol. 5, pp. 497-508.
Bumcrot et al., "RNAi therapeutics: a potential new class of pharmaceutical drugs", Nature Chemical Biology, vol. 2, No. 12, Dec. 2006, pp. 711-719.
Busquets et al., "Cathepsin E is a specific marker of dysplasia in APC mouse intestine", Tumour Biology, vol. 27, No. 1, 2006, pp. 36-42.
Campo et al., "Cathepsin B expression in colorectal carcinomas correlates with tumor progression and shortened patient survival", American Journal of Pathology, vol. 145, No. 2, Aug. 1994, pp. 301-309.
Cartwright et al., "Cancer of the pancreas: are we making progress? A review of studies in the US Oncology Research Network", Cancer Control, vol. 15, No. 4, Oct. 2008, pp. 308-313.
Caruso et al., "Over-expression of cathepsin E and trefoil factor 1 in sessile serrated adenomas of the colorectum identified by gene expression analysis", Virchows Arch, vol. 454, No. 3, Mar. 2009, pp. 291-302.
Castanotto et al., "The promises and pitfalls of RNA-interference-based therapeutics", Nature, vol. 457, No. 7228, Jan. 22, 2009, pp. 426-433.
Celli JP et al., "Imaging and photodynamic therapy: mechanisms, monitoring, and optimization," Chem Rev, 2010, vol. 110, pp. 2795-2838.
Chain et al., "The Expression and Function of Cathepsin E in Dendritic Cells", The Journal of Immunology, vol. 174, No. 4, Feb. 15, 2005, pp. 1791-1800.
Chanana et al., "Interaction of polyelectrolytes and their composites with living cells", Nano Letters, vol. 5, No. 12, 2005, pp. 2605-2612.
Chang et al., "Lessons from Nature: microRNA-based shRNA libraries", Nature Methods, vol. 3, No. 9, Sep. 2006, pp. 707-714.
Chang et al., "Prostate-specific membrane antigen is produced in tumor-associated neovasculature", Clinical Cancer Research, vol. 5, No. 10, Oct. 1999, pp. 2674-2681.
Chari, "Detecting early pancreatic cancer: problems and prospects", Seminars in Oncology, vol. 34, No. 4, Aug. 2007, pp. 284-294.
Check, "A tragic setback", Nature, vol. 420, No. 6912, Nov. 14, 2002, pp. 116-118.
Chen et al., "In vivo imaging of proteolytic activity in atherosclerosis", Circulation, vol. 105, No. 23, Jun. 11, 2002, pp. 2766-2771.
Chen et al., "Near-infrared fluorescent imaging of matrix metalloproteinase activity after myocardial infarction", Circulation, vol. 111, No. 14, Apr. 12, 2005, pp. 1800-1805.
Cho, "Understanding the Role of Surface Charges in Cellular Adsorption versus Internalization by Selectively Removing Gold Nanoparticles on the Cell Surface with a I2/KI Etchant", Nano Letters, vol. 9, No. 3, Mar. 11, 2009, pp. 1080-1084.
Choi et al., "Selective Antitumor Effect of Novel Protease-Mediated Photodynamic Agent", Cancer Research, vol. 66, No. 14, Jul. 15, 2006, pp. 7225-7229.
Choi Y et al., "Conjugation of a photosensitizer to an oligoarginine-based cell-penetrating peptide increases the efficacy of photodynamic therapy," ChemMedChem, 2006, vol. 1, pp. 458-463.
Choi Y et al., "Protease-mediated phototoxicity of a polylysine-chlorin(E6) conjugate," ChemMedChem, 2006, vol. 1, pp. 698-701.
Chu et al., "Aptamer: toxin conjugates that specifically target prostate tumor cells", Cancer Research, vol. 66, No. 12, Jun. 15, 2006, pp. 5989-5992.
Chua et al., "Pancreatic cancer—is the wall crumbling?", Annals of Oncology, vol. 19, No. 7, 2008, pp. 1224-1230.
Colella et al., "Increased cell density decreases cysteine proteinase inhibitor activity and increases invasive ability of two prostate tumor cell lines", Cancer Letters, vol. 185, No. 2, Nov. 28, 2002, pp. 163-172.
Crunkhorn, "RNA interference: clinical gene-silencing success", Nature Reviews Drug Discovery, vol. 9, May 2010, p. 359.
Cruz-Monserrate et al., "Detection of pancreatic cancer tumours and precursor lesions by cathepsin E activity in mouse models", Gut, vol. 61, No. 9, Sep. 2012, pp. 1315-1322.
Daniel et al., "Gold Nanoparticles: Assembly, Supramolecular Chemistry, Quantum-Size-Related Properties, and Applications toward Biology, Catalysis, and Nanotechnology", Chemical Reviews, vol. 104, No. 1, 2004, pp. 293-346.
Dassie et al., "Systemic administration of optimized aptamer-siRNA chimeras promotes regression of PSMA-expressing tumors", Nature Biotechnology, vol. 27, No. 9, 2009, pp. 839-849.

(56) References Cited

OTHER PUBLICATIONS

Davis et al., "Evidence of RNAi in humans from systemically administered siRNA via targeted nanoparticles", Nature, vol. 464, No. 7291, Apr. 15, 2010, pp. 1067-1070.
Declerck et al., "Proteases, extracellular matrix, and cancer: a workshop of the path B study section", American Journal of Pathology, vol. 164, No. 4, Apr. 2004, pp. 1131-1139.
Dhar et al., "Targeted delivery of cisplatin to prostate cancer cells by aptamer functionalized Pt(IV) prodrug-PLGA-PEG nanoparticles", Proceedings of the National Academy of Sciences of the USA, vol. 105, No. 45, Nov. 11, 2008, pp. 17356-17361.
Dolmans DE et al., "Photodynamic therapy for cancer," Nat Rev Cancer, 2003, vol. 3, pp. 380-387.
Dreyer et al., "Processing of the Pre-β-amyloid Protein by Cathepsin D is Enhanced by a Familial Alzheimer's Disease Mutation", European Journal of Biochemistry, vol. 224, No. 2, Sep. 1994, pp. 265-271.
Dunn, "A taste test for proteases", Nature Biotechnology, vol. 18, No. 2, Feb. 2000, pp. 149-150.
Edwards et al., "Cancer. Proteases—invasion and more", Nature, vol. 394, No. 6693, Aug. 6, 1998, pp. 527-528.
Elbakry et al., "Layer-by-Layer Assembled Gold Nanoparticles for siRNA Delivery", Nano Letters, vol. 9, No. 5, Mar. 30, 2009, pp. 2059-2064.
Elbashir et al., "Duplexes of 21-nucleotide RNAs mediate RNA interference in cultured mammalian cells", Nature, vol. 411, May 24, 2001, pp. 494-499.
Elouahabi et al., "Formation and Intracellular Trafficking of Lipoplexes and Polyplexes", Molecular Therapy, vol. 11, No. 3, Mar. 2005, pp. 336-347.
Eser et al., "In vivo diagnosis of murine pancreatic intraepithelial neoplasia and early-stage pancreatic cancer by molecular imaging", Proceedings of the National Academy of Science of the USA, vol. 108, No. 24, Jun. 14, 2011, pp. 9945-9950.
Evans et al. "Chemical imaging of tissue in vivo with video-rate coherent anti-Stokes Raman scattering microscopy," Proc. Natl. Acad. Sci.USA, 2005, vol. 102, No. 46, pp. 16807-16812.
Fan BG et al., "Photodynamic therapy for pancreatic cancer," Pancreas, 2007, vol. 34, pp. 385-389.
Farokhzad et al., "Nanoparticle-aptamer bioconjugates: a new approach for targeting prostate cancer cells", Cancer Research, vol. 64, No. 21, Nov. 1, 2004, pp. 7668-7672.
Fendrich et al., "Detection of Precursor Lesions of Pancreatic Adenocarcinoma in PET-CT in a Genetically Engineered Mouse Model of Pancreatic Cancer", Neoplasia, vol. 13, No. 2, Feb. 2011, pp. 180-186.
Fernandez et al., "Expression of cathepsins B and S in the progression of prostate carcinoma", International Journal of Cancer, vol. 95, No. 1, Jan. 20, 2001, pp. 51-55.
Finzi et al., "Cathepsin E in follicle associated epithelium of intestine and tonsils: localization to M cells and possible role in antigen processing", Histochemistry, vol. 99, No. 3, Mar. 1993, pp. 201-211.
Fire et al., "Potent and specific genetic interference by double-stranded RNA in Caenorhabditis elegans", Nature, vol. 391, No. 6669, Feb. 19, 1998, pp. 806-811.
Flores et al., "Detection of pancreatic carcinomas by imaging lactose-binding protein expression in peritumoral pancreas using [18F]fluoroethyl-deoxylactose PET/CT", PLoS One, vol. 4, No. 11, 2009, p. e7977.
Foltmann et al., In Handbook of Proteolytic Enzymes (Barrett, A.J., Rawlings, N.D. and Woessner, J.F., eds.), Academic Press, San Diego, 1998, pp. 819-823.
Frosch, "Molecular regulation, membrane association and secretion of tumor cathepsin B", APMIS, vol. 107, No. 1-6, Mar. 1999, pp. 28-37.
Fujimoto et al., "Layer-by-layer assembly of small interfering RNA and poly(ethyleneimine) for substrate-mediated electroporation with high efficiency", Analytical & Bioanalytical Chemistry, vol. 397, No. 2, May 2010, pp. 571-578.
Funovics et al., "Protease sensors for bioimaging", Analytical & Bioanalytical Chemistry, vol. 377, No. 6, Nov. 2003, pp. 956-963.
Gaind et al., "Deep-tissue imaging of intramolecular fluorescence resonance energy-transfer parameters," Opt. Letters, 2010, vol. 35, No. 9, pp. 1314-1316.
Gao et al., "Nonviral methods for siRNA delivery", Molecular Pharmaceutics, vol. 6, No. 3, May/Jun. 2009, pp. 651-658.
Gary et al., "Polymer-based siRNA delivery: perspectives on the fundamental and phenomenological distinctions from polymer-based DNA delivery", Journal of Controlled Release, vol. 121, No. 1-2, Aug. 16, 2007, pp. 64-73.
Ghosh et al., "Tumor target prostate specific membrane antigen (PSMA) and its regulation in prostate cancer", Journal of Cellular Biochemistry, vol. 91, No. 3, Feb. 15, 2004, pp. 528-539.
Giljohann, "Gene regulation with polyvalent siRNA-nanoparticle conjugates", Journal of the American Chemical Society, vol. 131, No. 6, Feb. 18, 2009, pp. 2072-2073.
Giljohann et al., "Gold Nanoparticles for Biology and Medicine", Angewandte Chemie International Edition, vol. 49, No. 19, Apr. 26, 2010, pp. 3280-3294.
Glondu, "A mutated cathepsin-D devoid of its catalytic activity stimulates the growth of cancer cells", Oncogene, vol. 20, No. 47, Oct. 18, 2001, pp. 6920-6929.
Goggins, "Identifying molecular markers for the early detection of pancreatic neoplasia", Seminars in Oncology, vol. 34, No. 4, Aug. 2007, pp. 303-310.
Goggins, "Markers of pancreatic cancer: working toward early detection", Clinical Cancer Research, vol. 17, No. 4, Feb. 15, 2011, pp. 635-637.
Gold et al., "Diversity of oligonucleotide functions", Annual Review of Biochemistry, vol. 64, 1995, pp. 763-797.
Gong et al., "Prostate-specific membrane antigen (PSMA)-specific monoclonal antibodies in the treatment of prostate and other cancers", Cancer Metastasis Reviews, vol. 18, No. 4, 1999, pp. 483-490.
Gounaris et al., "Live imaging of cysteine-cathepsin activity reveals dynamics of focal inflammation, angiogenesis, and polyp growth", PloS One, vol. 3, No. 8, Aug. 13, 2008, p. e2916.
Gulnik et al., "Design of sensitive fluorogenic substrates for human cathepsin D", Federation of European Biochemical Societies Letters, vol. 413, No. 2, Aug. 18, 1997, pp. 379-384.
Gutt et al., "Adjuvant radiotherapy for resected pancreatic cancer: a lack of benefit or a lack of adequate trials?", Nature Clinical Practice Gastroenterology and Hepatology, vol. 6, No. 1, Jan. 2009, pp. 38-46.
Haffner et al., "Prostate-specific membrane antigen expression in the neovasculature of gastric and colorectal cancers", Human Pathology, vol. 40, No. 12, Dec. 2009, pp. 1754-1761.
Hahn SM et al., "Photofrin uptake in the tumor and normal tissues of patients receiving intraperitoneal photodynamic therapy," Clin Cancer Res, 2006, vol. 12, pp. 5464-5470.
Harsha et al., "A compendium of potential biomarkers of pancreatic cancer", PLoS Medicine, vol. 6, No. 4, Apr. 7, 2009, p. e1000046.
Hawes et al., "A multispecialty approach to the diagnosis and management of pancreatic cancer", American Journal of Gastroenterology, vol. 95, No. 1, Jan. 2000, pp. 17-31.
Henry et al., "A prostate-specific membrane antigen-targeted monoclonal antibody-chemotherapeutic conjugate designed for the treatment of prostate cancer", Cancer Research, vol. 64, No. 21, Nov. 1, 2004, pp. 7995-8001.
Higashi et al., "Layer-by-layer fabrication of well-packed gold nanoparticle assemblies guided by a β-sheet peptide network", Polymer Journal, vol. 42, 2010, pp. 95-99.
Hingorani et al., "Preinvasive and invasive ductal pancreatic cancer and its early detection in the mouse", Cancer Cell, vol. 4, No. 6, Dec. 2003, pp. 437-450.
Ho et al., "Development of a dual fluorogenic and chromogenic dipeptidyl peptidase IV substrate", Bioorganic & Medicinal Chemistry Letters, vol. 16, No. 10, May 15, 2006, pp. 2599-2602.
Hon et al., "The roles of binding site arrangement and combinatorial targeting in microRNA repression of gene expression", Genome Biology, vol. 8, No. 8, 2007, p. R166.

(56) References Cited

OTHER PUBLICATIONS

Hopper C., "Photodynamic therapy: a clinical reality in the treatment of cancer," Lancet Oncol, 2000, vol. 1, pp. 212-219.

Hu et al., "Low Molecular Weight Polyethylenimine Conjugated Gold Nanoparticles as Efficient Gene Vectors", Bioconjugate Chemistry, vol. 21, No. 5, 2010, pp. 836-843.

Huguet et al., "Chemoradiotherapy in the management of locally advanced pancreatic carcinoma: a qualitative systematic review", Journal of Clinical Oncology, vol. 27, No. 13, May 1, 2009, pp. 2269-2277.

Hutvagner et al., "Argonaute proteins: key players in RNA silencing", Nature Review Molecular Cell Biology, vol. 9, No. 1, Jan. 2008, pp. 22-32.

Issa MC et al., "Photodynamic therapy: a review of the literature and image documentation," An Bras Dermatol, 2010, vol. 85, pp. 501-511.

Izuishi et al., "Impact of 18-fluorodeoxyglucose positron emission tomography on the management of pancreatic cancer", Journal of Gastrointestinal Surgery, vol. 14, No. 7, Jul. 2010, pp. 1151-1158.

Jackson et al., "Analysis of lung tumor initiation and progression using conditional expression of oncogenic K-ras", Genes and Development, vol. 15, No. 24, Dec. 15, 2001, pp. 3243-3248.

Jaffer et al., "In vivo imaging of thrombin activity in experimental thrombi with thrombin-sensitive near-infrared molecular probe", Arteriosclerosis, Thrombosis, and Vascular Biology, vol. 22, No. 11, Nov. 1, 2002, pp. 1929-1935.

Jang B et al., "Gold nanorod-photosensitizer complex for near-infrared fluorescence imaging and photodynamic/photothermal therapy in vivo," ACS Nano, 2011, vol. 5, pp. 1086-1094.

Jemal et al., "Cancer statistics, 2008", CA: A Cancer Journal for Clinicians, vol. 58, No. 2, 2008, pp. 71-96.

Jemal et al., "Cancer statistics, 2010", CA: A Cancer Journal for Clinicians, vol. 60, No. 5, Sep./Oct. 2010, pp. 277-300.

Jewell et al., "Multilayered polyelectrolyte assemblies as platforms for the delivery of DNA and other nucleic acid-based therapeutics", Advanced Drug Delivery Reviews, vol. 60, No. 9, 2008, pp. 979-999.

Ji et al., "Ras activity levels control the development of pancreatic diseases", Gastroenterology, vol. 137, No. 3, Sep. 2009, pp. 1072-1082.

Jinek et al., "A three-dimensional view of the molecular machinery of RNA interference", Nature, vol. 457, No. 7228, Jan. 22, 2009, pp. 405-412.

John et al., "Human MicroRNA targets", PLoS Biology, vol. 2, No. 11, Nov. 2004, p. e363.

Jonkers et al., "Synergistic tumor suppressor activity of BRCA2 and p53 in a conditional mouse model for breast cancer", Nature Genetics, vol. 29, No. 4, Dec. 2001, pp. 418-425.

Josephson et al., "High-efficiency intracellular magnetic labeling with novel superparamagnetic-Tat peptide conjugates", Bioconjugate Chemistry, vol. 10, No. 2, Mar./Apr. 1999, pp. 186-191.

Juliano et al., "Biological barriers to therapy with antisense and siRNA oligonucleotides", Molecular Pharmaceutics, vol. 6, No. 3, May/Jun. 2009, pp. 686-695.

Jupp et al., "Identification of the aspartic proteinases from human erythrocyte membranes and gastric mucosa (slow-moving proteinase) as catalytically equivalent to cathepsin E", Biochemical Journal, vol. 254, No. 3, Sep. 15, 1988, pp. 895-898.

Jupp et al., "The selectivity of statine-based inhibitors against various human aspartic proteinases", Biochemical Journal, vol. 265, No. 3, Feb. 1, 1990, pp. 871-878.

Just et al. "Optical coherence tomography allows for the reliable identification of laryngeal epithelial dysplasia and for precise biopsy: a clinicopathological study of 61 patients undergoing microlaryngoscopy" Laryngoscope, 2010, vol. 120, No. 10, pp. 1964-1970.

Kageyama et al., "A Cathepsin D-Like Acid Proteinase from Human Gastric Mucosa: Purification and Characterization", The Journal of Biochemistry, vol. 87, No. 3, Mar. 1989, pp. 737-743.

Kageyama, "Procathepsin E and cathepsin E", Methods in Enzymology, vol. 248, 1995, pp. 120-136.

Kageyama , "Rabbit procathepsin E and cathepsin E : Nucleotide sequence of cDNA, hydrolytic specificity for biologically active peptides and gene expression during development", European Journal of Biochemistry, vol. 216, No. 3, Sep. 1993, pp. 717-728.

Kakehashi et al., "Differential Regulation of the Nature and Functions of Dendritic Cells and Macrophages by Cathepsin E", The Journal of Immunology, vol. 179, No. 9, Nov. 1, 2007, pp. 5728-5737.

Kaul et al., "HIV protease inhibitors: advances in therapy and adverse reactions, including metabolic complications", Pharmacotherapy, vol. 19, No. 3, Mar. 1999, pp. 281-298.

Ke et al., "Optimal subsite occupancy and design of a selective inhibitor of urokinase", Journal of Biological Chemistry, vol. 272, No. 33, 1997, pp. 20456-20462.

Kelly et al., "Targeted nanoparticles for imaging incipient pancreatic ductal adenocarcinoma", PLoS Medicine, vol. 5, No. 4, 2008, p. e85.

Kennedy JC et al., "Photodynamic therapy with endogenous protoporphyrin IX: basic principles and present clinical experience," J Photochem Photobiol B, 1990, vol. 6, pp. 143-148.

Khan et al., "Cathepsin B and tumor-associated laminin expression in the progression of colorectal adenoma to carcinoma.", Modern Pathology, vol. 11, No. 8, Aug. 1998, pp. 704-708.

Kichler, "Gene transfer with modified polyethylenimines", Journal of Gene Medicine, vol. 6, Suppl. 1, Feb. 2004, pp. S3-S10.

Kim et al., "Generation of orthotopic and heterotopic human pancreatic cancer xenografts in immunodeficient mice", Nature Protocols, vol. 4, No. 11, 2009, pp. 1670-1680.

Kim et al., "Strategies for silencing human disease using RNA interference", Nature Reviews Genetics, vol. 8, No. 3, Mar. 2007, pp. 173-184.

Kim et al., "Strategies for targeted nonviral delivery of siRNAs in vivo", Trends in Molecular Medicine, vol. 15, No. Nov. 2009, pp. 491-500.

Kisiday et al., "Self-assembling peptide hydrogel fosters chondrocyte extracellular matrix production and cell division: implications for cartilage tissue repair", Proceedings of the National Academy of Sciences of the USA, vol. 99, No. 15, Jul. 23, 2002, pp. 9996-10001.

Kitamura, "Development of Systemic in vitro Evolution and Its Application to Generation of Peptide-Aptamer-Based Inhibitors of Cathepsin E", Journal of Molecular Biology, vol. 387, No. 5, Apr. 17, 2009, pp. 1186-1198.

Koblinski et al., "Unraveling the role of proteases in cancer", Clinical Chimica Acta, vol. 291, No. 2, Feb. 15, 2000, pp. 113-135.

Kokame, K. et al., "FRETS-VWF73, a first fluorogenic substrate for ADAMTS12 assay," Brit. J. Haematology, 2005, 129:93-100.

Konan YN et al., "State of the art in the delivery of photosensitizers for photodynamic therapy," J Photochem Photobiol B, 2002, vol. 66, pp. 89-106.

Krek et al., "Combinatorial microRNA target predictions", Nature Genetics, vol. 37, No. 5, May 2005, pp. 495-500.

Krishna et al., "EUS/EUS-FNA for suspected pancreatic cancer: influence of chronic pancreatitis and clinical presentation with or without obstructive jaundice on performance characteristics", Gastrointestinal Endoscopy, vol. 70, No. 1, Jul. 2009, pp. 70-79.

Kumar et al., "T Cell-Specific siRNA Delivery Suppresses HIV-1 Infection in Humanized Mice", Cell, vol. 134, No. 4, Aug. 22, 2008, pp. 577-586.

Kunath et al., "Low-molecular-weight polyethylenimine as a non-viral vector for DNA delivery: comparison of physicochemical properties, transfection efficiency and in vivo distribution with high-molecular-weight polyethylenimine", Journal of Controlled Release, vol. 89, No. 1, Apr. 14, 2003, pp. 113-125.

Kwan et al., "Grassystatins A-C from Marine Cyanobacteria, Potent Cathepsin E Inhibitors That Reduce Antigen Presentation", Journal of Medicinal Chemistry, vol. 52, No. 18, Sep. 24, 2009, pp. 5732-5747.

Kyte et al., "A simple method for displaying the hydropathic character of a protein", Journal of Molecular Biology, vol. 157, No. 1, May 5, 1982, pp. 105-132.

(56) References Cited

OTHER PUBLICATIONS

Ladror et al., "Cleavage at the amino and carboxyl termini of Alzheimer's amyloid-beta by cathepsin D", Journal of Biological Chemistry, vol. 269, No. 28, Jul. 15, 1994, pp. 18422-18428.
Lai et al., "Early diagnosis of osteoarthritis using cathepsin B sensitive near-infrared fluorescent probes", Osteoarthritis and Cartilage, vol. 12, No. 3, Mar. 2004, pp. 239-244.
Law et al., "A mitochondrial targeted fusion peptide exhibits remarkable cytotoxicity", Molecular Cancer Therapeutics, vol. 5, No. 8, Aug. 2006, pp. 1944-1949.
Law et al., "Design, Synthesis, and Characterization of Urokinase Plasminogen-Activator-Sensitive Near-Infrared Reporter", Chemistry & Biology, vol. 11, No. 1, Jan. 2004, pp. 99-106.
Law et al., "Optical zymography for specific detection of urokinase plasminogen activator activity in biological samples", Analytical Biochemistry, vol. 338, No. 1, Mar. 1, 2005, pp. 151-158.
Law et al., "Peptide-based biomaterials for protease-enhanced drug delivery", Biomacromolecules, vol. 7, No. 4, 2006, pp. 1261-1265.
Law et al., "Proteolysis: a biological process adapted in drug delivery, therapy, and imaging", Bioconjugate Chemistry, vol. 20, No. 9, Sep. 2009, pp. 1683-1695.
Ledakis et al., "Cathepsins D, B, and L in malignant human lung tissue", Clinical Cancer Research, vol. 2, No. 3, Mar. 1996, pp. 561-568.
Lee et al., "All-in-one target-cell-specific magnetic nanoparticles for simultaneous molecular imaging and siRNA delivery", Angewandte Chemie International Edition, vol. 48, No. 23, 2009, pp. 4174-4179.
Lee et al., "Layered nanoprobe for long-lasting fluorescent cell label", Small, vol. 8, No. 21, Nov. 5, 2012, pp. 3315-3320.
Lee, S.K. et al., "Effective Gene Silencing by multilayered siRNA coated gold nanoparticles," Small, 2011, vol. 7, No. 3, pp. 364-370.
Leguen et al., "Bioactive coatings based on polyelectrolyte multilayer architectures functionalized by embedded proteins, peptides or drugs", Biomolecular Engineering, vol. 24, No. 1, Feb. 2007, pp. 33-41.
Lewin et al., "Tat peptide-derivatized magnetic nanoparticles allow in vivo tracking and recovery of progenitor cells", Nature Biotechnology, vol. 18, No. 4, Apr. 2000, pp. 410-414.
Lewis et al., "The absence of p53 promotes metastasis in a novel somatic mouse model for hepatocellular carcinoma", Molecular and Cellular Biology, vol. 25, No. 4, Feb. 2005, pp. 1228-1237.
Lin et al., "Novel near-infrared cyanine fluorochromes: synthesis, properties, and bioconjugation", Bioconjugate Chemistry, vol. 13, No. 3, May/Jun. 2002, pp. 605-610.
Liu CD et al., "Hypericin and photodynamic therapy decreases human pancreatic cancer in vitro and in vivo," J Surg Res, 2000, vol. 93, pp. 137-143.
Liu et al., "Peptide-based molecular beacons for cancer imaging and therapy", Amino Acids, vol. 41, No. 5, Nov. 2011, pp. 1123-1134.
Loos et al., "Surgical treatment of pancreatic cancer", Annals of the NY Academy of Sciences, vol. 1138, Sep. 2008, pp. 169-180.
Lovell JF et al., "Activatable photosensitizers for imaging and therapy," Chem Rev, 2010, vol. 110, pp. 2839-2857.
Lu et al., "Covalently linked DNA/protein multilayered film for controlled DNA release", Journal of Colloid and Interface Science, vol. 314, No. 1, Oct. 1, 2007, pp. 80-88.
Lupold et al., "Identification and characterization of nuclease-stabilized RNA molecules that bind human prostate cancer cells via the prostate-specific membrane antigen", Cancer Research, vol. 62, No. 14, Jul. 15, 2002, pp. 4029-4033.
Mackay et al., "A Possible Role for Cathepsins D, E, and B in the Processing of β-amyloid Precursor Protein in Alzheimer's Disease", European Journal of Biochemistry, vol. 244, No. 2, Mar. 1997, pp. 414-425.
Mallikaratchy et al., "Cell specific aptamer-photosensitizer conjugates as a molecular tool in photodynamic therapy", ChemMedChem, vol. 3, No. 3, Mar. 2008, pp. 425-428.

Mansouri, "Modulating the release kinetics through the control of the permeability of the layer-by-layer assembly: a review", Expert Opinion on Drug Delivery, vol. 6, No. 6, Jun. 2009, pp. 585-597.
Marecos et al., "Antibody-mediated versus nontargeted delivery in a human small cell lung carcinoma model", Bioconjugate Chemistry, vol. 9, No. 2, Mar./Apr. 1998, pp. 184-191.
Marten et al., "Detection of dysplastic intestinal adenomas using enzyme-sensing molecular beacons in mice", Gastroenterology, vol. 122, No. 2, Feb. 2002, pp. 406-414.
Matsuo et al., "Immunohistochemical localization of cathepsins D and E in human gastric cancer: A possible correlation with local invasive and metastatic activities of carcinoma cells", Human Pathology, vol. 27, No. 2, Feb. 1996, pp. 184-190.
Mayya et al., "Preparation and Organization of Nanoscale Polyelectrolyte-Coated Gold Nanoparticles", Advanced Functional Materials, vol. 13, No. 3, Mar. 2003, pp. 183-188.
McCawley et al., "Matrix metalloproteinases: multifunctional contributors to tumor progression", Molecular Medicine Today, vol. 6, No. 4, Apr. 1, 2000, pp. 149-156.
McIntyre et al., "Molecular imaging of proteolytic activity in cancer", Journal of Cellular Biology, vol. 90, No. 6, Dec. 15, 2003, pp. 1087-1097.
McNamara et al., "Cell type-specific delivery of siRNAs with aptamer-siRNA chimeras", Nature Biotechnology, vol. 24, No. 8, 2006, pp. 1005-1015.
Medarova et al., "In vivo imaging of siRNA delivery and silencing in tumors", Nature Medicine, vol. 13, No. 3, Mar. 2007, pp. 372-377.
Meister et al., "Mechanisms of gene silencing by double-stranded RNA", Nature, vol. 431, No. 7006, Sep. 16, 2004, pp. 343-349.
Messerli et al., "A novel method for imaging apoptosis using a caspase-1 near-infrared fluorescent probe", Neoplasia, vol. 6, No. 2, Mar./Apr. 2004, pp. 95-105.
Mitelman et al., "The impact of translocations and gene fusions on cancer causation", Nature Reviews Cancer, vol. 7, No. 4, Apr. 2007, pp. 233-245.
Mota et al., "Cathepsin E expression by normal and premalignant cervical epithelium", American Journal of Pathology, vol. 150, No. 4, Apr. 1997, pp. 1223-1229.
Murphy et al., "Current evaluation of the tissue localization and diagnostic utility of prostate specific membrane antigen", Cancer, vol. 83. No. 11, Dec. 1, 1998, pp. 2259-2269.
Musiol R et al., "Prodrugs in photodynamic anticancer therapy," Curr Pharm Des, 2011, vol. 17, pp. 3548-3559.
Muto et al., "Characteristic Distribution of Cathepsin E Which Immunologically Cross-Reacts with the 86-kDa Acid Proteinase from Rat Gastric Mucosa", The Journal of Biochemistry, vol. 103, No. 4, Apr. 1988, pp. 629-632.
Muto et al., "Purification and properties of a cathepsin D-like acid proteinase from rat gastric mucosa", Biochimica et Biophysica Acta (BBA)—Protein Structure and Molecular Enzymology, vol. 745, No. 1, May 30, 1983, pp. 61-69.
Nakanishi et al., "Increased Expression of Cathepsins E and D in Neurons of the Aged Rat Brain and Their Colocalization with Lipofuscin and Carboxy-Terminal Fragments of Alzheimer Amyloid Precursor Protein", Journal of Neurochemistry, vol. 68, No. 2, Feb. 1997, pp. 739-749.
Nishikawa et al., "The role of cathepsin B and cystatin C in the mechanisms of invasion by ovarian cancer", Gynecologic Oncology, vol. 92, No. 3, Mar. 2004, pp. 881-886.
Nishioka NS, "Drug, light, and oxygen: a dynamic combination in the clinic," Gastroenterology, 1998, vol. 114, pp. 604-606.
Nomura et al., "Involvement of cathepsins in the invasion, metastasis and proliferation of cancer cells", Journal of Medical Investigation, vol. 52, No. 1-2, Feb. 2005, pp. 1-9.
Olive et al., "The use of targeted mouse models for preclinical testing of novel cancer therapeutics", Clinical Cancer Research, vol. 12, No. 18, Sep. 15, 2006, pp. 5277-5287.
Parsons et al., "Preoperative evaluation of pancreatic adenocarcinoma", Journal of Hepatobiliary Pancreatic Surgery, vol. 15, No. 4, 2008, pp. 429-435.
Peiper et al., "Human Pancreatic Cancer Cells (MPANC-96) Recognized by Autologous Tumor-Infiltrating Lymphocytes After in

(56) References Cited

OTHER PUBLICATIONS

Vitro as Well as in Vivo Tumor Expansion", International Journal of Cancer, vol. 71, No. 6, Jun. 11, 1997, pp. 993-999.

Peng Q et al., "5-Aminolevulinic acid-based photodynamic therapy. Clinical research and future challenges," Cancer, 1997, vol. 79, pp. 2282-2308.

Peterson CM et al., "HPMA copolymer delivery of chemotherapy and photodynamic therapy in ovarian cancer," Adv Exp Med Biol, 2003, vol. 519, pp. 101-123.

Peyratout et al., "Tailor-Made Polyelectrolyte Microcapsules: From Multilayers to Smart Containers", Angewandte Chemie International Edition, vol. 43, No. 29, Jul. 19, 2004, pp. 3762-3783.

Pham et al., "Developing a peptide-based near-infrared molecular probe for protease sensing", Bioconjugate Chemistry, vol. 15, No. 6, Nov./Dec. 2004, pp. 1403-1407.

Podgorski, "Bone microenvironment modulates expression and activity of cathepsin B in prostate cancer", Neoplasia, vol. 7, No. 3, Mar. 2005, pp. 207-223.

Prasad et al., "Gene expression profiles in pancreatic intraepithelial neoplasia reflect the effects of Hedgehog signaling on pancreatic ductal epithelial cells", Cancer Research, vol. 65, No. 5, Mar. 1, 2005, pp. 1619-1626.

Qin et al., "Inhibiting HIV-1 infection in human T cells by lentiviral-mediated delivery of small interfering RNA against CCR5", Proceedings of the National Academy of Sciences of the USA, vol. 100, No. 1, Jan. 7, 2003, pp. 183-188.

Qiu et al., "Environment-sensitive hydrogels for drug delivery", Advances in Drug Delivery Reviews, vol. 53, No. 3, Dec. 31, 2001, pp. 321-339.

Rabbitts, "Commonality but diversity in cancer gene fusions", Cell, vol. 137, No. 3, May 1, 2009, pp. 391-395.

Rao et al., "Specificity in the binding of inhibitors to the active site of human/primate aspartic proteinases: analysis of P2—P1—P1'—P2' variation", Journal of Medicinal Chemistry, vol. 36, No. 18, 1993, pp. 2614-2620.

Rao-Naik et al., "Exploring the binding preferences/specificity in the active site of human cathepsin E", Proteins, vol. 22, No. 2, Jun. 1995, pp. 168-181.

Read et al., "A versatile reducible polycation-based system for efficient delivery of a broad range of nucleic acids", Nucleic Acids Research, vol. 33, No. 9, May 2005, p. e86.

Regula J et al., "Photodynamic therapy using 5-aminolaevulinic acid for experimental pancreatic cancer—prolonged animal survival," Br J Cancer, 1994, vol. 70, pp. 248-254.

Reynolds et al., "Protamine as an efficient membrane-translocating peptide", Bioconjugate Chemistry, vol. 16, No. 5, 2005, pp. 1240-1245.

Rocha-Lima, "New directions in the management of advanced pancreatic cancer: a review", Anticancer Drugs, vol. 19, No. 5, Jun. 2008, pp. 435-446.

Rochefort et al., "Cathepsin D in cancer metastasis: A protease and a ligand", Apmis, vol. 107, No. 1-6, Mar. 1999, pp. 86-95.

Rosi et al., "Oligonucleotide-modified gold nanoparticles for intracellular gene regulation", Science, vol. 312, No. 5776, May 19, 2006, pp. 1027-1030.

Rubin et al., "Bioinformatics approach leads to the discovery of the TMPRSS2:ETS gene fusion in prostate cancer", Laboratory Investigations, vol. 86, No. 11, Nov. 2006, pp. 1099-1102.

Sakai et al., "Quantitation and immunohistochemical localization of cathepsins E and D in rat tissues and blood cells", Biochimica et Biophysica Acta (BBA)—General Subjects, vol. 991, No. 2, May 31, 1989, pp. 367-375.

Sastradipura et al., "Identification of Cellular Compartments Involved in Processing of Cathepsin E in Primary Cultures of Rat Microglia", The Journal of Neurochemistry, vol. 70, No. 5, May 1998, pp. 2045-2056.

Scarborough et al., "Exploration of subsite binding specificity of human cathepsin D through kinetics and rule-based molecular modeling", Protein Science, vol. 2, No. 2, Feb. 1993, pp. 264-276.

Scarborough et al., "Redesign of the substrate specificity of human cathepsin D: the dominant role of position 287 in the S2 subsite", Protein Engineering Design & Selection, vol. 7, No. 4, Apr. 1994, pp. 495-502.

Schneider et al., "Multifunctional Cytotoxic Stealth Nanoparticles. A Model Approach with Potential for Cancer Therapy", Nano Letters, vol. 9, No. 2, Feb. 2009, pp. 636-642.

Schultz et al., "Mobile Near-Infrared Fluorescence Imaging: New Tissue Resection Guidance Tool for Surgeons", www.siemens.com/medical-magazine, Dec. 2007, 8 pages.

Scorilas et al., "Determination of cathepsin B expression may offer additional prognostic information for ovarian cancer patients", Biological Chemistry, vol. 383, No. 7-8, Jul./Aug. 2002, pp. 1297-1303.

Sessa et al., "Ductal cancers of the pancreas frequently express markers of gastrointestinal epithelial cells", Gastroenterology, vol. 98, No. 6, Jun. 1990, pp. 1655-1665.

Shah et al., "In Vivo Imaging of HIV Protease Activity in Amplicon Vector-transduced Gliomas", Cancer Research, vol. 64, No. 1, Jan. 1, 2004, pp. 273-278.

Shah et al., "Inducible release of TRAIL fusion proteins from a proapoptotic form for tumor therapy", Cancer Research, vol. 64, No. 9, May 1, 2004, pp. 3236-3242.

Siegel R et al., "Cancer statistics, 2012," CA Cancer J Clin, 2012, vol. 62, pp. 10-29.

Singh et al., "Poly-l-lysine-coated albumin nanoparticles: Stability, mechanism for increasing in vitro enzymatic resilience, and siRNA release characteristics", Acta Biomaterialia, vol. 6, No. 11, Nov. 2010, pp. 4277-4284.

Sinha et al., "Cathepsin B in angiogenesis of human prostate: an immunohistochemical and immunoelectron microscopic analysis", The Anatomical Record, vol. 241, No. 3, Mar. 1995, pp. 353-362.

Sinha et al., "Immunohistochemical localization of cathepsin B in neoplastic human prostate", Prostate, vol. 26, No. 4, Apr. 1995, pp. 171-178.

Sinha et al., "Plasma membrane association of cathepsin B in human prostate cancer: biochemical and immunogold electron microscopic analysis", Prostate, vol. 49, No. 3, Nov. 1, 2001, pp. 172-184.

Smith et al., "Synthetic peptide-based DNA complexes for nonviral gene delivery", Advanced Drug Delivery Reviews, vol. 30, No. 1-3, 1998, pp. 115-131.

Song et al., "Gold nanoparticles capped with polyethyleneimine for enhanced siRNA delivery", Small, vol. 6, No. 2, Jan. 2010, pp. 239-246.

Sun et al., "Novel targets for therapeutic intervention against ischemic brain injury", Clinical Neuropharmacology, vol. 22, No. 3, May/Jun. 1999, pp. 164-171.

Tai et al., "Inhibition of Breast Cancer Cell Growth and Invasiveness by Dual Silencing of HER-2 and VEGF", Molecular Pharmaceutics, vol. 7, No. 2, Apr. 5, 2010, pp. 543-556.

Tang, In Handbook of Proteolytic Enzymes (Barrett, A.J., Rawlings, N.D. and Woessner, J.F., eds.), Academic Press, San Diego, 1998, pp. 828-836.

Tatematsu et al., "Markers of surface mucous cell type human gastric cancer cells: galactose oxidase-Schiff reactive mucins, monoclonal antibody SH-9 reactive mucins and cathepsin E", Acta Pathologica Japonica, vol. 43, No. 9, Sep. 1993, pp. 500-506.

Tenti et al., "Cervical adenocarcinomas express markers common to gastric, intestinal, and pancreatobiliary epithelial cells", Pathology, Research and Practice, vol. 190, No. 4, Apr. 1994, pp. 342-349.

Terris et al., "Characterization of Gene Expression Profiles in Intraductal Papillary-Mucinous Tumors of the Pancreas", American Journal of Pathology, vol. 160, No. 5, May 2002, pp. 1745-1754.

Thomas et al., "Conjugation to gold nanoparticles enhances polyethylenimine's transfer of plasmid DNA into mammalian cells", Proceedings of the National Academy of Sciences of the USA, vol. 100, No. Jun. 12, 2003, pp. 9138-9143.

Tiemann et al., "You have full text access to this OnlineOpen article RNAi-based therapeutics—current status, challenges and prospects", EMBO Molecular Medicine, vol. 1, No. 3, Jun. 2009, pp. 142-151.

(56) References Cited

OTHER PUBLICATIONS

Tomlins et al., "Distinct classes of chromosomal rearrangements create oncogenic ETS gene fusions in prostate cance", Nature, vol. 448, No. 7153, Aug. 2, 2007, pp. 595-599.
Tomlins et al., "Recurrent fusion of TMPRSS2 and ETS transcription factor genes in prostate cancer", Science, vol. 310, No. 5748, Oct. 28, 2005, pp. 644-648.
Topazian M et al., "Photodynamic therapy of intraductal papillary mucinous neoplasm," Endoscopy, 2012, vol. 44, pp. 213-215.
Torchilin et al., "TAT peptide on the surface of liposomes affords their efficient intracellular delivery even at low temperature and in the presence of metabolic inhibitors", Proceedings of the National Academy of Sciences of the USA, vol. 98, No. 15, Jul. 17, 2001, pp. 8786-8791.
Tsukuba , "Association of cathepsin E deficiency with development of atopic dermatitis", Journal of Biochemistry, vol. 134, No. 6, Dec. 2003, pp. 893-902.
Tung et al., "A Novel Near-Infrared Fluorescence Sensor for Detection of Thrombin Activation in Blood", Chembiochem, vol. 3, No. 2-3, Mar. 1, 2002, pp. 207-211.
Tung et al., "Arginine containing peptides as delivery vectors", Advanced Drug Delivery Reviews, vol. 55, No. 2, Feb. 10, 2003, pp. 281-294.
Tung et al., "In Vivo Imaging of Proteolytic Enzyme Activity Using a Novel Molecular Reporter", Cancer Research, vol. 60, No. 17, Sep. 1, 2000, pp. 4953-4958.
Tung et al., "Novel branching membrane translocational peptide as gene delivery vector", Bioorganic & Medicinal Chemistry, vol. 10, No. 11, Nov. 2002, pp. 3609-3614.
Tung et al., "Preparation of a Cathepsin D Sensitive Near-Infrared Fluorescence Probe for Imaging", Bioconjugate Chemistry, vol. 10, No. 5, Sep. 1999, pp. 892-896.
Ueno et al., "Adjuvant treatments for resectable pancreatic cancer", Journal of Hepatobiliary Pancreatic Surgery, vol. 15, No. 5, Sep. 2008, pp. 468-472.
Ullmann et al., "Protein expression profiles in adenocarcinomas and squamous cell carcinomas of the lung generated using tissue microarrays", Journal of Pathology, vol. 203, No. 3, Jul. 2004, pp. 798-807.
Uno et al., "Clinical significance of cathepsin E in pancreatic juice in the diagnosis of pancreatic ductal adenocarcinoma", Journal of Gastroenterology and Hepatology, vol. 15, No. 11, Nov. 2000, pp. 1333-1338.
Urban-Klein et al., "RNAi-mediated gene-targeting through systemic application of polyethylenimine (PEI)—complexed siRNA in vivo", Gene Therapy, vol. 12, No. 5, Mar. 2005, pp. 461-466.
Van Geel IP et al., "Mechanisms for optimising photodynamic therapy: second-generation photosensitisers in combination with mitomycin C," Br J Cancer, 1995, vol. 72, pp. 344-350.
Varadarajulu et al., "Yield of EUS-guided FNA of pancreatic masses in the presence or the absence of chronic pancreatitis", Gastrointestinal Endoscopy, vol. 62, No. 5, Nov. 2005, pp. 728-736.
Verma et al., "Effect of surface properties on nanoparticle—cell interactions", Small, vol. 6, No. 1, Jan. 4, 2010, pp. 12-21.
Von Burstin et al., "Highly sensitive detection of early-stage pancreatic cancer by multimodal near-infrared molecular imaging in living mice", International Journal of Cancer, vol. 123, No. 9, Nov. 1, 2008, pp. 2138-2147.
Waghray et al., "Analysis of a truncated form of cathepsin H in human prostate tumor cells", Journal of Biological Chemistry, vol. 277, No. 13, Mar. 29, 2002, pp. 11533-11538.
Waley et al., "The action of trypsin on polylysine", Biochemical Journal, vol. 55, No. 2, Sep. 1953, pp. 328-337.
Wang et al., "Design and synthesis of new fluorogenic HIV protease substrates based on resonance energy transfer", Tetrahedron Letters, vol. 31, No. 45, 1990, pp. 6493-6496.
Wang et al., "Pleiotropic biological activities of alternatively spliced TMPRSS2/ERG fusion gene transcripts", Cancer Research, vol. 68, No. 20, Oct. 15, 2008, pp. 8516-8524.
Wang et al., "Superparamagnetic iron oxide nanoparticle-aptamer bioconjugates for combined prostate cancer imaging and therapy", ChemMedChem, vol. 3, No. 9, Sep. 15, 2008, pp. 1311-1315.
Weissleder et al., "In vivo imaging of tumors with protease-activated near-infrared fluorescent probes", Nature Biotechnology, vol. 17, No. 4, Apr. 1999, pp. 375-378.
Weissleder et al., "Non-invasive in vivo mapping of tumour vascular and interstitial volume fractions", European Journal of Cancer, vol. 34, No. 9, Aug. 1998, pp. 1448-1454.
Wild et al., "Gene expression profiling of progressive papillary noninvasive carcinomas of the urinary bladder", Clinical Cancer Research, vol. 11, No. 12, Jun. 15, 2005, pp. 4415-4429.
Wullner et al., "Cell-specific induction of apoptosis by rationally designed bivalent aptamer-siRNA transcripts silencing eukaryotic elongation factor 2", Current Cancer Drug Targets, vol. 8, No. 7, Nov. 2008, pp. 554-565.
Wunder et al., "In vivo imaging of protease activity in arthritis: a novel approach for monitoring treatment response", Arthritis and Rheumatism, vol. 50, No. 8, Aug. 2004, pp. 2459-2465.
Xie Q et al., "Synergetic anticancer effect of combined gemcitabine and photodynamic therapy on pancreatic cancer in vivo," World J Gastroenterol, 2009, vol. 15, pp. 737-741.
Xiong et al., "Periodicity of polar and nonpolar amino acids is the major determinant of secondary structure in self-assembling oligomeric peptides", Proceedings of the National Academy for Sciences of the USA, vol. 92, No. 14, Jul. 3, 1995, pp. 6349-6353.
Yamamoto et al., "Affinity Purification and Properties of Cathepsin-E-Like Acid Proteinase from Rat Spleen", European Journal of Biochemistry, vol. 92, No. 2, Dec. 1978, pp. 499-508.
Yang et al., "Molecular imaging of pancreatic cancer in an animal model using targeted multifunctional nanoparticles", Gastroenterology, vol. 136, No. 5, May 2009, pp. 1514-1525e2.
Yasuda et al., "A new selective substrate for cathepsin E based on the cleavage site sequence of $\alpha 2$-macroglobulin", Biological Chemistry, vol. 386, No. 3, Mar. 2005, pp. 299-305.
Yasuda et al., "Characterization of New Fluorogenic Substrates for the Rapid and Sensitive Assay of Cathepsin E and Cathepsin D", Journal of Biochemistry, vol. 125, No. 6, Jun. 1999, pp. 1137-1143.
Yeo et al., "Six hundred fifty consecutive pancreaticoduodenectomies in the 1990s: pathology, complications, and outcomes", Annals of Surgery, vol. 226, No. 3, Sep. 1997, pp. 248-260.
Yoshimine et al., "Specific immunocytochemical localization of cathepsin E at the ruffled border membrane of active osteoclasts", Cell and Tissue Research, vol. 281, No. 1, Jul. 1995, pp. 85-91.
Yusuf TE et al., "EUS-guided photodynamic therapy with verteporfin for ablation of normal pancreatic tissue: a pilot study in a porcine model (with video)," Gastrointest Endosc, 2008, vol. 67, pp. 957-961.
Zaidi et al., "A new approach for distinguishing cathepsin E and D activity in antigen-processing organelles", Federation of European Biochemical Societies Journal, vol. 274, No. 12, Jun. 2007, pp. 3138-3149.
Zaidi et al., "Cathepsin E: a mini review", Biochemical and Biophysical Research Communications, vol. 367, No. 3, Mar. 14, 2008, pp. 517-522.
Zaidi et al., "Emerging Functional Roles of Cathepsin E", Biochemical and Biophysical Research Communications, vol. 377, No. 2, 2008, pp. 327-330.
Zaidi et al., "Recombinant cathepsin E has no proteolytic activity at neutral pH", Biochemical and Biophysical Research Communications, vol. 360, No. 1, Aug. 17, 2007, pp. 51-55.
Zamore, "RNA interference: big applause for silencing in Stockholm", Cell, vol. 127, No. Dec. 15, 2006, pp. 1083-1086.
Zhang et al., "Cationic lipids and polymers mediated vectors for delivery of siRNA", Journal of Controlled Release, vol. 123, No. 1, Oct. 18, 2007, pp. 1-10.
Zhang et al., "Construction of a novel chimera consisting of a chelator-containing Tat peptide conjugated to a morpholino antisense oligomer for technetium-99m labeling and accelerating cellular kinetics", Nuclear Medicine and Biology, vol. 33, No. 2, Feb. 2006, pp. 263-269.
Tomari et al., "Perspective: machines for RNAi", Genes & Development, vol. 19, No. 5, Mar. 1, 2005, pp. 517-529.

(56) References Cited

OTHER PUBLICATIONS

Zhang et al., "SiRNA-loaded multi-shell nanoparticles incorporated into a multilayered film as a reservoir for gene silencing", Biomaterials, vol. 31, No. 23, Aug. 2010, pp. 6013-6018.

Zhang et al., "Using an RNA aptamer probe for flow cytometry detection of CD30-expressing lymphoma cells", Laboratory Investigation, vol. 89, No. 12, Dec. 2009, pp. 1423-1432.

\* cited by examiner

COMPOSITIONS AND METHODS FOR USING CATHEPSIN E CLEAVABLE SUBSTRATES

CROSS-REFERENCE TO RELATED APPLICATIONS

This application claims priority to provisional U.S. Ser. No. 61/764,314, filed Feb. 13, 2013, which is incorporated by reference herein in its entirety.

STATEMENT REGARDING FEDERALLY FUNDED RESEARCH

This invention was made under government Grant No. R01 CA135312 from the National Institutes of Health. The government has certain rights to this invention.

BACKGROUND

Pancreatic ductal adenocarcinoma (PDAC) remains a devastating disease. In the U.S., PDAC is the fourth leading cause of cancer death, with average survival of less than 1 year from diagnosis. To date, surgery has been the only curative treatment; however, only 20% of patients are candidates for surgical resection. Moreover, subsets of patients who initially appear to have resectable tumors are subsequently found to have locally advanced disease, in which a margin-negative resection is not feasible. Unfortunately, no effective treatments for locally invasive and metastatic PDAC are known at this time.

Optionally, prodrugs can be used in the treatment of cancer. Prodrugs are compounds that are administered in an inactive or less than fully active form. These compounds are then processed or converted to an active therapeutic agent through normal metabolic processes. Prodrugs are sometimes referred to as precursors as they serve as a type of precursor to the intended active therapeutic agent.

Currently, photodynamic therapy (PDT) is a widely accepted treatment modality for many cancerous and precancerous lesions, including those in bladder, brain, ovary, and skin. It is a minimally invasive treatment that damages the target cells by imparting cytotoxicity through generation of reactive oxygen species. The individual PDT components, including photosensitizer (PS), light, and oxygen, are nontoxic. However, upon illumination of the light-sensitive PS in the presence of oxygen, highly reactive singlet oxygen ($^1O_2$) species are generated within the tumor tissue, causing severe damage to all cells in the vicinity of the treated area. Although the intravenously administrated photosensitizers accumulate in the intended tumor tissue, they also undergo non-specific distribution to non-target tissues, resulting in unavoidable damage to the normal cells. Therefore, the patients must avoid light for a long period until the concentration of the sensitizer decreases to an acceptable level.

SUMMARY

Provided herein are compositions and kits comprising a therapeutic agent linked to a cleavable substrate, wherein the cleavable substrate is capable of being cleaved by cathepsin E. The compositions and kits described herein optimize administration of an agent to a specific location and for a specific duration. Thus, provided herein are methods of treating one or more symptoms of a disease or disorder characterized by expression of cathepsin E in a subject and methods of eliminating a cancer cell characterized by expression of cathepsin E using the provided compositions and kits. Further provided herein are methods of detecting the presence of a cancer cell or detecting a cathepsin E expressing cell using a photosensitizer linked to a cleavable substrate, wherein the cleavable substrate is capable of being cleaved by cathepsin E.

The details of one or more embodiments are set forth in the accompanying drawings and the description below. Other features, objects, and advantages of the invention will be apparent from the description and drawings, and from the claims.

DESCRIPTION OF DRAWINGS

FIG. 1A shows representative microscopic images of unfixed human pancreatic cancer cells (MPanc96-CTSE) after treatment with 0.5 µM 5-ALA (5-aminolevulinic acid) prodrug (panels a, b) and free 5-ALA as a positive control (panels c, d). Cells imaged on an inverted epifluorescence microscope in bright field (top) and TRITC (Tetramethyl Rhodamine isothiocyanate) channel ($\lambda$ex=557 nm, $\lambda$em=576 nm) (bottom). Images show significant fluorescence signals originating from cells treated with the 5-ALA prodrug, comparable to that obtained with free 5-ALA, indicating the efficient release of 5-ALA from the prodrug. FIG. 1B shows representative microscopic images of unfixed PDAC cells expressing Cath E (MPanc96-CTSE) (panels a, b) and parent cell line (MPanc96-FG30) (panels c, d) after treatment with 0.5 µM 5-ALA prodrug for 1 hour at 37° C. The pronounced fluorescence signal observed within the MPanc96-CTSE cells indicates strong Cath E-mediated release of 5-ALA, which enables visualization of cells in the TRITC channel (panel b). In contrast, MPanc96-FG30 cells, with limited Cath E expression, failed to show an appreciable fluorescence signal, strongly suggesting the lack of free 5-ALA within the cells (panel d).

FIG. 3A are photomicrographs showing human pancreatic cancer cells, MPanc96-FG30 (left) and MPanc96-CTSE (right), treated with 0.1 µM 5-ALA prodrug after light exposure (10 J/cm2). The images show morphological changes in MPanc96-CTSE cells and, to a lesser extent, in the parental MPanc96-FG30 cells, which have limited expression of Cath E. This strongly suggests that the enzymatic activity of Cath E plays a major role in the efficiency of treatment. FIG. 3B is a graph showing viability of MPanc-FG30 and MPanc96-CTSE cells treated with light dose of 2.5 J/cm2 with various concentrations (0.1, 0.5, 1, and 5 µM) of 5-ALA prodrug. Quantitation of cell viability demonstrated that the PDT was more highly phototoxic in MPanc96-CTSE, compared to Mpanc-FG30, cells under all conditions. FIG. 3C is a bar graph showing viability of MPanc96-CTSE cells treated with a range of light doses (2.5, 5, 10, and 15 J/cm2) at various concentrations (0.1, 0.5, 1, and 5 μM) of 5-ALA prodrug. Quantitation of cell viability illustrated that the phototoxic effect of PDT on the cells increased with increasing concentration of 5-ALA prodrug and light dose.

FIG. 6A is a schematic showing the general structure of intact 5-ALA prodrug and its metabolic fragments observed upon enzymatic degradation with Cath E. FIG. 6B is a graph showing mass spectrometric characterization of intact 5-ALA prodrug and its metabolites after Cath E digestion. The sequence of the cleavable substrate (SEQ ID NO:1) is shown.

FIG. 7A is a graph showing fragment ions (monoisotopic masses) detected in high-energy MS-MS spectra. FIG. 7B is a fragment ion table based on the monoisotopic masses.

DETAILED DESCRIPTION

Figure 1A:
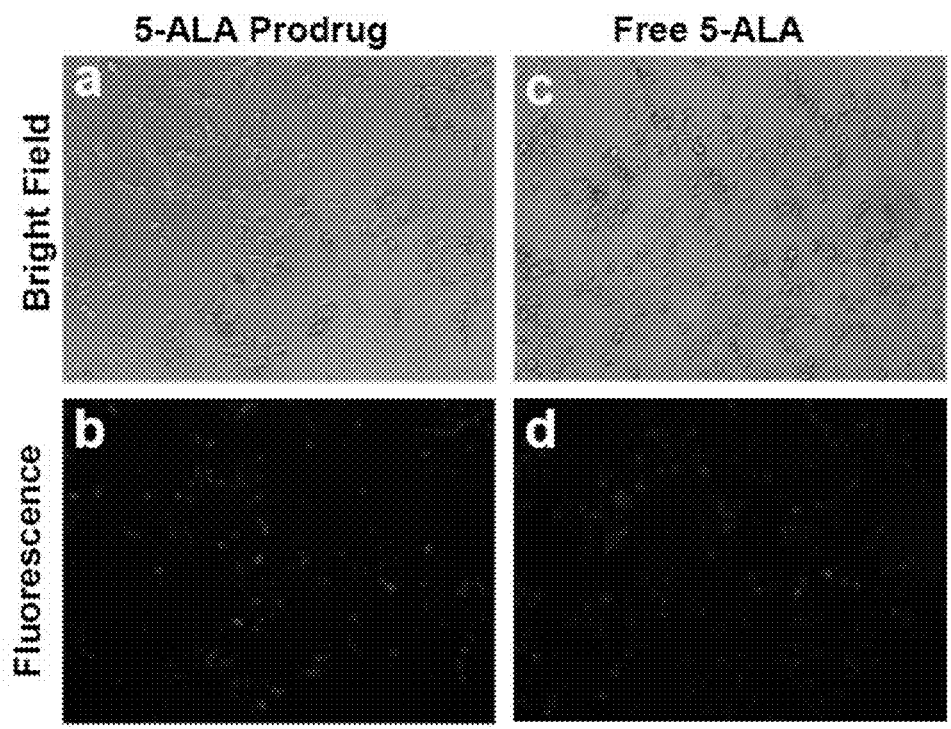
FIGS. 1A and 1B are photomicrographs showing the 5-ALA prodrug is efficiently activated by Cath E-expressing PDAC cells.

A variety of photosensitizers (PSs) have been used clinically. 5-aminolevulinic acid (5-ALA), which has no photosensitivity itself, is a precursor for the in situ biosynthesis of protoporphyrin IX (PpIX), an essential intermediate of hemoglobin synthesis and a natural PS. 5-ALA has been used in the clinic, due to its suitability as a tumor-imaging agent and its efficacy in PDT. However, parallel accumulation of 5-ALA in both malignant and normal cells has hindered efforts to implement its use. In addition to 5-ALA, other non-specific photosensitizers, including hypericin, photosan, meso-tetrahydroxyphenyl chlorine, verteporfin, and porfimer sodium, also have been tested in PDAC. In all cases, the non-specificity of the PS caused adverse side effects. Enhancing the discriminatory ability of the administered PS is key to confining the PDT effect to the tumor tissue and minimizing unwanted damage to normal tissues in close proximity.

Cathepsin E (Cath E) is overexpressed in human PDAC, both in early lesions of PDAC, called pancreatic intraepithelial neoplasias (PanINs), as well as in metastases (Cruz-Monserrate et al., Gut 61:1315-22 (2012)). Described herein is a 5-ALA residue incorporated at the end of a scissile peptide that has selective Cath E cleavage susceptibility. This conjugation of 5-ALA and a Cath E substrate peptide overcomes the non-specificity of 5-ALA. Thus, the present application describes the development and validation of compositions and methods for controlled release of agents specifically within the Cath E-rich tumor environment, but not in normal tissue, for site-specific targeting of the cancerous tissues, with minimal impairment to the contiguous normal tissues.

Provided is a composition including a therapeutic agent linked to a cleavable substrate, wherein the cleavable substrate is capable of being cleaved by cathepsin E. Suitable therapeutic agents for use in the provided compositions include, but are not limited to, photosensitizers and chemotherapeutic agents. As used throughout, photosensitizers include agents that render a substance, cell or organism sensitive to the influence of radiant energy or light. Photosensitizers are generally nontoxic light-sensitive agents that, when exposed to light, become toxic to diseased cells. The term photosensitizer includes photosensitizer precursors that are converted within the body or within a cell to become active light-sensitive agents. Photosensitizers include, for example, porphyrins and chlorins. Examples of photosensitizers suitable for use in the provided compositions include, but are not limited to, hypericin, photosan, meso-tetrahydroxyphenyl chlorine, 5-aminolevulini acid (5-ALA), Rose Bengal, bacteriochlorin, hematoporphyrin, chlorin e6, tetraphenylporphyrin, benzoporphyrin, verteporfin, and porfimer sodium. Examples of chemotherapeutic agents suitable for use in the provided compositions include, but are not limited to, gemcitabine, fluorouracil, erlotinib hydrochloride, mitomycin C, doxorubicin, irinotecan, cytoxan, eloxatin, prednisone, vinorelbine, carboplatin, and taxotere.

The provided compositions are suitable for formulation and administration in vitro or in vivo. Optionally, the compositions comprise one or more of the provided therapeutic agents linked to a cleavable substrate and a pharmaceutically acceptable carrier. Suitable carriers and their formulations are described in *Remington: The Science and Practice of Pharmacy*, 21$^{st}$ *Edition*, David B. Troy, ed., Lippicott Williams & Wilkins (2005). By pharmaceutically acceptable carrier is meant a material that is not biologically or otherwise undesirable, i.e., the material is administered to a subject without causing undesirable biological effects or interacting in a deleterious manner with the other components of the pharmaceutical composition in which it is contained. If administered to a subject, the carrier is optionally selected to minimize degradation of the active ingredient, sustain or delay its release, and to minimize adverse side effects in the subject.

The compositions can be administered in a number of ways as selected by one skilled in the art and depending on whether local or systemic treatment is desired, on the target area to be treated, and other variables. The compositions are administered via any of several routes of administration, including topically, orally, parenterally, intravenously, intra-articularly, intraperitoneally, intramuscularly, subcutaneously, intracavity, transdermally, intrahepatically, intracranially, nebulization/inhalation, or by installation via bronchoscopy.

Preparations for parenteral administration include sterile aqueous or non-aqueous solutions, suspensions, and emulsions. Examples of non-aqueous solvents are propylene glycol, polyethylene glycol, oils, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's, or fixed oils. Intravenous vehicles include fluid and nutrient replenishers, electrolyte replenishers (such as those based on Ringer's dextrose), and the like. Preservatives and other additives are optionally present such as, for example, antimicrobials, anti-oxidants, chelating agents, and inert gases and the like.

Formulations for topical administration include ointments, lotions, creams, gels, drops, suppositories, sprays, liquids, and powders. Conventional pharmaceutical carriers, aqueous, powder, or oily bases, thickeners and the like are optionally necessary or desirable.

Compositions for oral administration include powders or granules, suspension or solutions in water or non-aqueous media, capsules, sachets, or tables. Thickeners, flavorings, diluents, emulsifiers, dispersing aids or binders are optionally used.

Compositions can be formulated to provide quick, sustained or delayed release after administration by employing procedures known in the art. Certain carriers may be more preferable depending upon, for instance, the route of administration and concentration of composition being administered. Suitable formulations for use in the provided compositions can be found in *Remington: The Science and Practice of Pharmacy*, 21$^{st}$ Edition, David B. Troy, ed., Lippicott Williams & Wilkins (2005).

As described herein, therapeutic agents for use in the provided methods and compositions are targeted to cells associated with a disease or disorder characterized by expression of Cathepsin E through the use of a cleavable substrate capable of being cleaved by Cathepsin E. Therapeutic agents can be in active, partially active, inactive, or partially inactive forms. Optionally, the therapeutic agent is further processed, e.g., within a cell, into an active or partially active form, for example, as in the case of a precursor or prodrug that is subsequently processed within a cell into an active or partially active therapeutic agent. The therapeutic agents are linked to the cleavable substrate and cleavage of the substrate in the targeted cells releases the therapeutic agent, resulting in reduction or elimination of the targeted cells. Suitable cleavable substrates capable of being cleaved by Cathepsin E include, but are not limited to, Arg-Gln-Ala-Gly-Phe-Ser-Leu (SEQ ID NO:1), Gln-Ala-Gly-Phe-Ser-Leu (SEQ ID NO:2), Ala-Gly-Phe-Ser-Leu (SEQ ID NO:3), Gly-Phe-Ser-Leu (SEQ ID NO:4), Phe-Ser-Leu (SEQ ID NO:5), Ser-Leu (SEQ ID NO:6), Arg-Gln-Ala-Gly-Phe-Ser-Phe (SEQ ID NO:7), Gln-Ala-Gly-Phe-Ser-Phe (SEQ ID NO:8), Ala-Gly-Phe-Ser-Phe (SEQ ID NO:9), Gly-Phe-Ser-Phe (SEQ ID NO:10), Phe-Ser-Phe (SEQ ID NO:11), Ser-Phe (SEQ ID NO:12), Ala-Gln-Ala-Gly-Phe-Ser-Leu-Pro-Ala (SEQ ID NO:13), Gln-Ala-Gly-Phe-Ser-Leu-Pro-Ala (SEQ ID NO:14), Ala-Gly-Phe-Ser-Leu-Pro-Ala (SEQ ID NO:15), Gly-Phe-Ser-Leu-Pro-Ala (SEQ ID NO:16), Phe-Ser-Leu-Pro-Ala (SEQ ID NO:17), Ser-Leu-Pro-Ala (SEQ ID NO:18), and Ser-Leu-Pro (SEQ ID NO:19).

Also provided are methods of treating one or more symptoms of a disease or disorder characterized by expression of cathepsin E in a subject. The methods include the steps of selecting a subject with a disease or disorder characterized by expression of cathepsin E and administering to the subject an effective amount of a therapeutic agent linked to a cleavable substrate, wherein the cleavable substrate is capable of being cleaved by cathepsin E. Administration of the effective amount of the therapeutic agent linked to the cleavable substrate to the subject treats or reduces one or more symptoms of the disease or disorder characterized by expression of cathepsin E. Further provided are methods of eliminating a cancer cell characterized by expression of cathepsin E. The method includes the steps of contacting the cell with an effective amount of a therapeutic agent linked to a cleavable substrate, wherein the cleavable substrate is capable of being cleaved by cathepsin E and wherein administration of the effective amount results in elimination of the cancer cell. Optionally, the therapeutic agent is a photosensitizer or a chemotherapeutic agent. Examples of photosensitizers suitable for use in the provided methods include, but are not limited to, porphyrins, chlorins, hypericin, photosan, meso-tetrahydroxyphenyl chlorine, 5-aminolevulini acid (5-ALA), Rose Bengal, bacteriochlorin, hematoporphyrin, chlorin e6, tetraphenylporphyrin, benzoporphyrin, verteporfin, and porfimer sodium.

Examples of chemotherapeutic agents suitable for use in the provided methods include, but are not limited to, gemcitabine, fluorouracil, erlotinib hydrochloride, mitomycin C, doxorubicin, irinotecan, cytoxan, eloxatin, prednisone, vinorelbine, carboplatin, and taxotere. In the provided methods, the cleavable substrate is cleaved by cathepsin E to separate the cleavable substrate and the therapeutic agent.

Optionally, the subject or cell is exposed to a light source having a wavelength suitable to activate the photosensitizer. Optionally, the step of exposing the subject to a light source comprises exposing cells in the subject associated with the disease or disorder to light having a wavelength suitable to activate the photosensitizer. Activation of the photosensitizer results in the death of cells associated with the disease or disorder. The subject or cell is exposed to a light source under conditions suitable for activation of the photosensitizer. Suitable light sources include, but are not limited to, lasers, e.g., diode lasers; fluorescent lamps; dichroic lamps; very bright, full-spectrum light sources; or light-emitting diodes. The subject or cell is exposed to the light source for an amount of energy and/or time to achieve a desired effect, i.e., to result in elimination of cancer cells or reduction or treatment of one or more symptoms associated with a disease or disorder characterized by cathepsin E expression. Optionally, the subject or cell is exposed to 1 to 50 J/Cm$^2$ of light. The amount of light energy necessary to obtain effective results during photoirradiation (e.g., a first or second photoirradiation) can be pre-determined by evaluating the effective amounts for particular subjects, types of subjects, photosensitizers, light source, location or target cells, and/or formulations. The amount of light energy can also be regulated in response to feedback during treatment. For example, the amount of light being delivered can be regulated based on concurrent analysis of photosensitizer penetration, heat level in the tissue, or the level of discomfort being experienced by the subject.

Optionally, the disease or disorder characterized by expression of cathepsin E is cancer. Optionally, the cancer is pancreatic cancer, cervical cancer, gastric cancer, prostate cancer, colorectal cancer, breast cancer, adenoendocrine cancer, and lung cancer. Optionally, the pancreatic cancer is pancreactic ductal adenocarcinoma.

The provided compositions can further include an additional or second therapeutic agent. Similarly, the provided methods can further comprise administering to the subject an additional or second therapeutic agent suitable for treating one or more symptoms of the disease or disorder characterized by expression of cathepsin E. Optionally, the disease is cancer and the additional therapeutic agent is a chemotherapeutic agent. Exemplary chemotherapeutic agents that can be used as additional or second therapeutic agents in the provided method include, but are not limited to, bleomycin, carboplatin, chlorambucil, cisplatin, colchicine, cyclophosphamide, daunorubicin, dactinomycin, diethylstilbestrol doxorubicin, etoposide, 5-fluorouracil, floxuridine, gemcitabine, erlotinib hydrochloride, irinotecan, cytoxan, eloxatin, prednisone, vinorelbine, melphalan, methotrexate, mitomycin, 6-mercaptopurine, taxotere, teniposide, 6-thioguanine, vincristine and vinblastine. Combinations of agents or compositions can be administered either concomitantly (e.g., as a mixture), separately but simultaneously (e.g., via separate intravenous lines) or sequentially (e.g., one agent is administered first followed by administration of the second agent). Thus, the term combination is used to refer to concomitant, simultaneous or sequential administration of two or more agents or compositions.

Provided herein are methods of detecting the presence of a cancer cell. The methods include the steps of contacting a cell with an effective amount of a photosensitizer linked to a cleavable substrate, wherein the cleavable substrate is capable of being cleaved by cathepsin E; exposing the cell to light having a wavelength suitable to activate the photosensitizer; and detecting the level of fluorescence of the photosensitizer. An increase in the level of fluorescence of the photosensitizer as compared to a control indicates the cell is a cancer cell. Also provided are methods of detecting a cathepsin E expressing cell. The methods include the steps of contacting a cell with an effective amount of a photosensitizer linked to a cleavable substrate, wherein the cleavable substrate is capable of being cleaved by cathepsin E; exposing the cell to light having a wavelength suitable to activate the photosensitizer; and detecting fluorescence of the photosensitizer. Fluorescence of the photosensitizer above background or as compared to a control indicates the cell is a cathepsin E expressing cell. Optionally, the cathepsin E expressing cell or cancer cell is in vitro or in vivo. Optionally, cathepsin E expressing cell is a cancer cell. In the aforementioned methods, the cancer cell is, for example, a pancreatic cancer cell. The cancer can be pancreatic cancer, cervical cancer, gastric cancer, prostate cancer, colorectal cancer, breast cancer, adenoendocrine cancer, or a lung cancer.

Optionally, the photosensitizer is, for example, a porphyrin or a chlorin. Examples of photosensitizers suitable for use in the provided methods include, but are not limited to, hypericin, photosan, meso-tetrahydroxyphenyl chlorine, 5-aminolevulini acid (5-ALA), Rose Bengal, bacteriochlorin, hematoporphyrin, chlorin e6, tetraphenylporphyrin, benzoporphyrin, verteporfin, and porfimer sodium. The photosensizers are linked to the cleavable substrate and cleavage of the substrate in the targeted cells releases the photosensitizer, resulting in detection of the cancer cell or cell expressing cathepsin E. As described above, suitable cleavable substrates capable of being cleaved by Cathepsin E include, but are not limited to, Arg-Gln-Ala-Gly-Phe-Ser-Leu (SEQ ID NO:1), Gln-Ala-Gly-Phe-Ser-Leu (SEQ ID NO:2), Ala-Gly-Phe-Ser-Leu (SEQ ID NO:3), Gly-Phe-Ser-Leu (SEQ ID NO:4), Phe-Ser-Leu (SEQ ID NO:5), Ser-Leu (SEQ ID NO:6), Arg-Gln-Ala-Gly-Phe-Ser-Phe (SEQ ID NO:7), Gln-Ala-Gly-Phe-Ser-Phe (SEQ ID NO:8), Ala-Gly-Phe-Ser-Phe (SEQ ID NO:9), Gly-Phe-Ser-Phe (SEQ ID NO:10), Phe-Ser-Phe (SEQ ID NO:11), Ser-Phe (SEQ ID NO:12), Ala-Gln-Ala-Gly-Phe-Ser-Leu-Pro-Ala (SEQ ID NO:13), Gln-Ala-Gly-Phe-Ser-Leu-Pro-Ala (SEQ ID NO:14), Ala-Gly-Phe-Ser-Leu-Pro-Ala (SEQ ID NO:15), Gly-Phe-Ser-Leu-Pro-Ala (SEQ ID NO:16), Phe-Ser-Leu-Pro-Ala (SEQ ID NO:17), Ser-Leu-Pro-Ala (SEQ ID NO:18), and Ser-Leu-Pro (SEQ ID NO:19).

The detecting step can comprise fluorescence microscopy and in vivo imaging methods like X-ray, MRI, and fluorescent imaging. Other techniques for diagnosing cancer via in vivo fluorescence imaging are known in the art. See, for example, Bourg et al., "A mouse model for monitoring calpain activity under physiological and pathological conditions," J. Biol. Chem. 22:281(51): 39672-80 (2006) and Kularatne et al., "Deep-tissue imaging of intramolecular fluorescence resonance energy-transfer parameters," Opt. Letters 35(9): 1314-6 (2010). Other techniques for in vivo diagnosis include, but are not limited to, MRI, optical coherence tomography (OCT) (see, for example, Lankenau et al. "Optical coherence tomography allows for the reliable identification of laryngeal epithelial dysplasia and for precise biopsy: a clinicopathological study of 61 patients undergoing microlaryngoscopy" Laryngoscope 120(10): 1964-70 (2010), and coherent anti-Stokes Raman scattering (CARS) endoscopy (see, for example, Evans et al. "Chemical imaging of tissue in vivo with video-rate coherent anti-Stokes Raman scattering microscopy," Proc. Natl. Acad. Sci. USA 102(46): 16807-12 (2005). One or more in vivo imaging techniques can be utilized to diagnose cancer in a subject. A sample can, for example, comprise cells or tissue isolated from the subject.

As used herein, control refers to a nondiseased cell from the same subject or a different subject. Optionally, control refers to a cell known not to express cathepsin E. Optionally, the level of fluorescence in a cell is compared to a known reference value or a value measured in a control cell. The known reference value can, for example, be from a nondiseased cell or a cell known not to express cathepsin E. Those of skill in the art are capable of determining the appropriate background levels and controls for detection of levels of fluorescence in cells.

Provided herein are kits comprising one or more of the provided compositions in one or more suitable containers. Optionally, the kits include instructions for use. Optionally, the kit comprises one or more doses of an effective amount of a composition comprising a therapeutic agent linked to a cleavable substrate. Optionally, the composition is present in a container such as a vial or packet. Optionally, the kit comprises one or more additional agents for treating or preventing one or more symptom of a disease or disorder characterized by expression of cathepsin E, e.g., cancer. Optionally, the kit further includes an additional or second therapeutic agent, e.g., a chemotherapeutic agent. The additional or second therapeutic agent may be included in the composition or formulated as a second composition. Optionally, the kit comprises a means of administering the compositions, such as, for example, a syringe, needle, tubing, catheter, patch, and the like. The kit may also comprise formulations and/or materials requiring sterilization and/or dilution prior to use.

As used throughout, a subject can be a vertebrate, more specifically a mammal (e.g., a human, horse, cat, dog, cow, pig, sheep, goat, mouse, rabbit, rat, and guinea pig), birds, reptiles, amphibians, fish, and any other animal. The term does not denote a particular age or sex. Thus, adult and newborn subjects, whether male or female, are intended to be covered. As used herein, patient or subject may be used interchangeably and can refer to a subject with a disease or disorder (e.g., cancer). The term patient or subject includes human and veterinary subjects.

In the provided methods, the therapeutic agent may be administered to a subject at a dosage of between about 0.01 mg/kg body weight to 1000 mg/kg body weight. Further, the compositions and kits can comprise a concentration of the therapeutic agent suitable for use in the provided methods. For example, the provided compositions and kits can comprise from 0.01 to 1000 mg of therapeutic agent. Optionally, the therapeutic agent may be administered to a subject at a dosage of about 10 mg/kg body weight to about 500 mg/kg body weight, or about 50 mg/kg body weight to about 250 mg/kg body weight, or about 100 mg/kg body weight to about 200 mg/kg body weight. The dosage that can be used in the provided methods can be any amount from 1 mg/kg body weight to 1000 mg/kg body weight inclusive. Optionally, the dosage of therapeutic agent that is administered to a subject is 20 mg/kg body weight. According to the methods taught herein, the subject is administered an effective amount of the agent. The terms effective amount and effective dosage are used interchangeably. The term effective amount is defined as any amount necessary to produce a desired physiologic response. Effective amounts and schedules for administering the agent may be determined empirically, and making such determinations is within the skill in the art. The dosage ranges for administration are those large enough to produce the desired effect in which one or more symptoms of the disease or disorder are affected (e.g., reduced or delayed). The dosage should not be so large as to cause substantial adverse side effects, such as unwanted cross-reactions, anaphylactic reactions, and the like. Generally, the dosage will vary with the age, condition, sex, type of disease, the extent of the disease or disorder, route of administration, or whether other drugs are included in the regimen, and can be determined by one of skill in the art. The dosage can be adjusted by the individual physician in the event of any contraindications. Dosages can vary, and can be administered in one or more dose administrations daily, for one or several days. Guidance can be found in the literature for appropriate dosages for given classes of pharmaceutical products.

As used herein the terms treatment, treat, or treating refers to a method of reducing the effects of one or more symptoms of a disease or condition characterized by expression of the protease or symptom of the disease or condition characterized by expression of the protease. Thus in the disclosed method, treatment can refer to a 10%, 20%, 30%, 40%, 50%, 60%, 70%, 80%, 90%, or 100% reduction in the severity of an established disease, condition, or symptom of the disease or condition. For example, a method for treating a disease is considered to be a treatment if there is a 10% reduction in one or more symptoms of the disease in a subject as compared to a control. Thus the reduction can be a 10%, 20%, 30%, 40%, 50%, 60%, 70%, 80%, 90%, 100%, or any percent reduction in between 10% and 100% as compared to native or control levels. It is understood that treatment does not necessarily refer to a cure or complete ablation of the disease, condition, or symptoms of the disease or condition. Further, as used herein, references to decreasing, reducing, or inhibiting include a change of 10%, 20%, 30%, 40%, 50%, 60%, 70%, 80%, 90% or greater as compared to a control level and such terms can include but do not necessarily include complete elimination.

Disclosed are materials, compositions, and components that can be used for, can be used in conjunction with, can be used in preparation for, or are products of the disclosed methods and compositions. These and other materials are disclosed herein, and it is understood that when combinations, subsets, interactions, groups, etc. of these materials are disclosed that while specific reference of each various individual and collective combinations and permutations of these compounds may not be explicitly disclosed, each is specifically contemplated and described herein. For example, if a method is disclosed and discussed and a number of modifications that can be made to a number of molecules including the method are discussed, each and every combination and permutation of the method, and the modifications that are possible are specifically contemplated unless specifically indicated to the contrary. Likewise, any subset or combination of these is also specifically contemplated and disclosed. This concept applies to all aspects of this disclosure including, but not limited to, steps in methods using the disclosed compositions. Thus, if there are a variety of additional steps that can be performed, it is understood that each of these additional steps can be performed with any specific method steps or combination of method steps of the disclosed methods, and that each such combination or subset of combinations is specifically contemplated and should be considered disclosed.

Publications cited herein and the material for which they are cited are hereby specifically incorporated by reference in their entireties.

A number of embodiments have been described. Nevertheless, it will be understood that various modifications may be made. Accordingly, other embodiments are within the scope of the claims below.

EXAMPLES

Example 1

Cathepsin E as a Drug Activator

Materials and Methods

Synthesis and Characterization of the 5-ALA Prodrug

The Cathepsin E-activatable 5-ALA prodrug, H-Arg-Gln-Ala-Gly-Phe-Ser-Leu-5-ALA-OH, was synthesized by solid-phase peptide synthesis (SPPS) using standard Fmoc chemistry with HBTU/HOBT coupling chemistry on an automatic synthesizer (Tribute, Protein Technologies, Tucson, Ariz.). The dipeptide Fmoc-Leu-5-ALA was first prepared in solution phase using 0.4N HCTU/NMM, purified by HPLC, and characterized by LC-MS using an LCQ Fleet mass spectrometer (Thermo Finnigan, West Palm Beach, Fla.). For better coupling efficiency, peptide chain elongation on 2-chlorotrityl chloride resin (0.1 mmole, 1.3 µmol/mg, Novabiochem, La Jolla, Calif.) was initiated by coupling the Fmoc-Leu-5-ALA-COOH dipeptide, followed by the rest of the amino acid residues. All protecting groups were removed and the peptide was cleaved from the resin using a deprotection-scavenger cocktail (TFA:DCM:

TIS=95:2.5:2.5, 10 mL/gm peptidyl resin) for three hours. After HPLC purification, the exact mass of the 5-ALA prodrug was confirmed by LC-MS. Enzymatic cleavage susceptibility was assessed by incubating the 5-ALA prodrug with Cath E, Cath D, or Cath B (50 pmole each) in 50 mM sodium acetate for 1 hour to achieve complete digestion, and then the fragments were identified by LC-MS.

Cell Lines and Cell Culture.

Two established pancreatic cancer cell lines, MPanc96-FG30 and MPanc96-CTSE, with low and high Cath E expression, respectively, were used in this study (Cruz-Monserrate et al., Gut 61:1315-22 (2012); Abd-Elgaliel, et al., Mol. Biosyst. 7:3207-13 (2011)). Both cell lines were cultured routinely in DMEM supplemented with 10% FBS and 1× Pen/Strep (100 U/mL penicillin, 100 µg/mL treptomycin). All cells were maintained at 37° C. in a humidified atmosphere of 5% $CO_2$.

Cellular Validation of Cathepsin E-Mediated Release of 5-ALA.

Mpanc96-CTSE and Mpanc96-FG30 cells ($1.2 \times 10^4$) were treated in 96-well plates with various concentrations (0.1, 0.5, 1, and 5 µM in 100 µL) of 5-ALA prodrug, incubated for 30 minutes at 37° C., and washed several times with PBS. Fluorescence images of the cells were acquired using an inverted epifluorescence microscope and a TRITC (tetramethyl rhodamine isothiocyanate) filter ($\lambda ex=557$ nm and $\lambda em=576$ nm). Free 5-ALA and untreated cells were included as controls. The possible light damage done in the absence of photosensitizer was evaluated by irradiating Cath E-positive Mpanc96-CTSE cells with various doses (2.5, 5, 10, 15, and 18 $J/cm^2$) of light using a diode laser system (652 nm; B&W TEK, Newark, Del.). Phototoxicity of the 5-ALA prodrug was assessed by incubating Mpanc96-CTSE and Mpanc96-FG30 cells in 96-well plates with 0.1 µM 5-ALA prodrug for 30 minutes at 37° C. The cells were washed several times with PBS, the medium was replaced with growth medium, and the cells were treated with a single dose of 10 J/cm2. After PDT, the treated cells and controls were incubated overnight followed by imaging to detect changes in cell morphology.

Cell Viability and Apoptotic Cell Damage Assays.

To determine the number of viable cells after light treatment, a homogeneous colorimetric method, the MTS Cell cytotoxicity assay (Cell Titer 96® $Aq_{ueous}$, Promega, Madison, Wis.) was used. MPanc96-CTSE and MPanc96-FG30 ($2 \times 10^4$) cells were incubated with various concentrations (0.1, 0.5, 1, and 5 µM) of the 5-ALA prodrug for 30 minutes, followed by treatment with a range of light doses (2.5, 5, 10, and 15 $J/cm^2$) and incubated overnight at 37° C. and 5% $CO_2$ in 96-well plates. Cells treated only with light or the 5-ALA prodrug were used as negative controls. To each well containing PDAC cells in 100 µL of phenol-free culture medium, 20 µL of MTS solution were added and the cells were incubated for 1 hour. The formation of colored formazan was measured directly in 96-well assay plates at 490 nm absorbance without additional processing. All assays were performed in triplicate. Membrane permeability and dead cell apoptosis assay kit (Life Technologies, Carlsbad, Calif.) were used for staining cells with YO-PRO-1 and propidium iodide (PI) dyes. After PDT, MPanc96-CTSE cells were washed with PBS buffer, treated with 1 µL YO-PRO-1 and PI stock solution per milliliter medium and incubated on ice for 25 minutes, followed by fluorescence imaging using an inverted epifluorescence microscope. Free 5-ALA was included as a positive control and untreated cells as a negative control.

Animal Preparation and In Vivo Photodynamic Therapy.

All animal studies were performed in compliance with the approved animal protocols and guidelines of Institutional Animal Care and Use Committee of University of Texas MD Anderson Cancer Center. Transgenic mice were genetically engineered to develop pancreatic cancer in 6-8 weeks after birth by crossing LSL-KRasG12D mice with floxed p53 mice and pancreatic specific cre (Pdx-1-Cre) mice to yield mice that possessed a conditional p53 deletion and endogenous mutant KRasG12D. Littermates without PDAC served as controls. LSL-KRasG12D, p53-floxed, and Pdx-1-Cre genetic mice were obtained from the Mouse Models for Human Cancer Consortium Repository (Rockville, Md.). Mice were divided into three groups of five transgenic mice with PDAC tumors and three normal littermate controls. Mice were injected with a single dose of saline, free 5-ALA, or the 5-ALA prodrug (1 mg 5-ALA equivalent/kg, 50 µL) intravenously through the tail vein using a 30 gauge needle. Mice were incubated for 60 minutes in a full metabolically active environment and anesthetized by intraperitoneal injection of sodium pentobarbital, at a dose of 50-90 mg/kg diluted to 6 mg/ml. The pancreas was exposed through a left abdominal incision (1 cm, laparotomy) and treated with a 10-$J/cm^2$ dose of light using a diode laser (652 nm) and incidence fluence rate of 50 $mW/cm^2$ for 3.5 minutes. After PDT, the pancreas was carefully returned to the peritoneal cavity and the abdomen was closed. One day after light treatment, animals were sacrificed and the pancreases were harvested for subsequent evaluation.

Histochemical Staining of Mouse Tissues.

Formalin-fixed and paraffin-embedded tissue sections of normal and cancerous pancreas were then examined for apoptosis by TUNEL (terminal deoxynucleotidyl transferase (TdT)-mediated deoxyuridine triphosphate-(dUTP-) biotin nick end labeling) staining using ApopTag® Peroxidase in situ apoptosis detection kit (EMD Millipore, Billerica, Mass.). Tissues included 5 samples of PDAC treated with 5-ALA precursor probe, 5 samples of PDAC treated with free 5-ALA as a positive control, and 5 samples of PDAC treated with normal saline as a negative control. Eight normal litter-control pancreas samples were included, including 3 samples of normal pancreas treated with the 5-ALA prodrug, 3 samples of normal pancreas treated with free 5-ALA, and 2 samples of normal pancreas treated with normal saline. Two tissue samples were treated with DNase for use as positive standards in the TUNEL assay.

Statistical Analysis.

Statistical Package (version 13, SPSS, Chicago, Ill.) was used to assess the statistical mean error using the paired-samples t-test with two-tailed p-values.

Results

5-ALA Prodrug is Efficiently Cleaved by Cath E In Vitro.

Figure 6A:
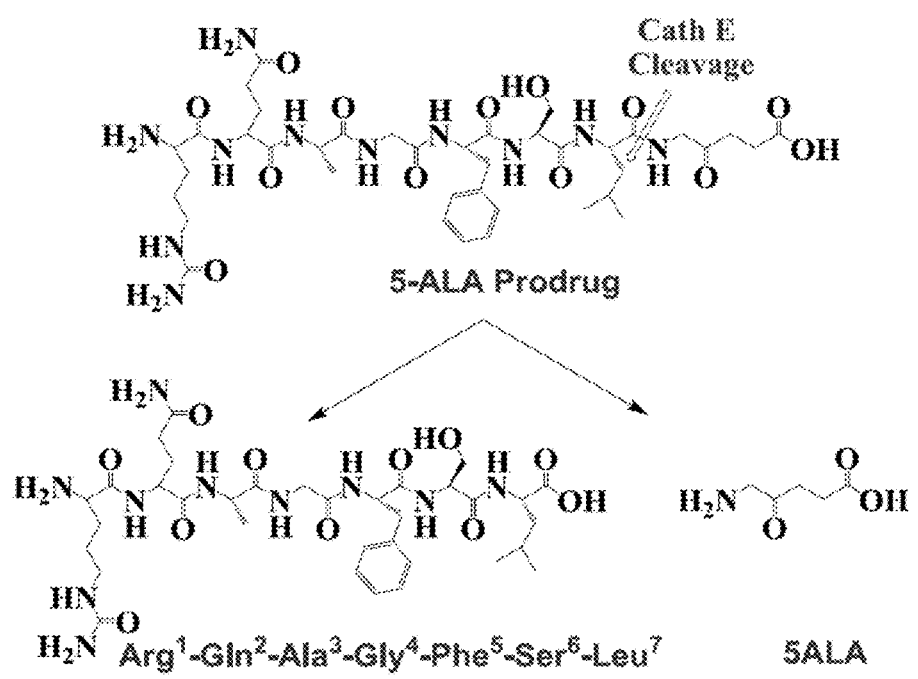
FIGS. 6A and 6B show the pathway for the 5-ALA prodrug designed to efficiently release free 5-ALA upon selective degradation.
Figure 6B:
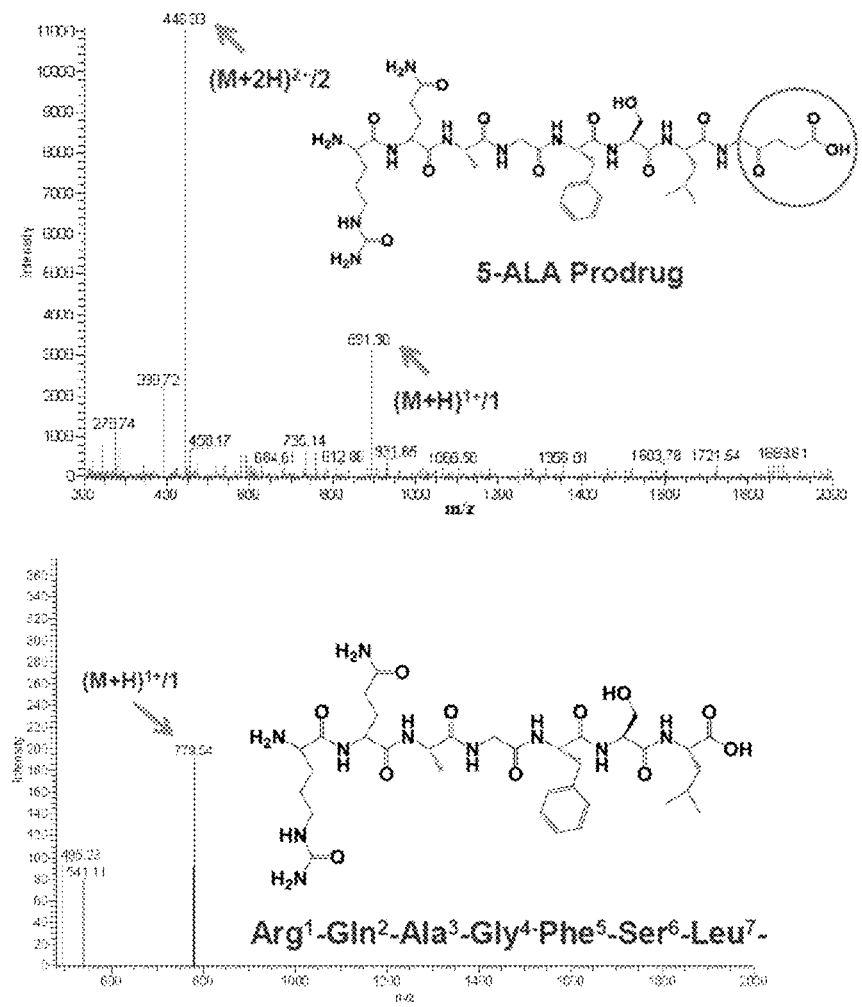
Figure 7A:
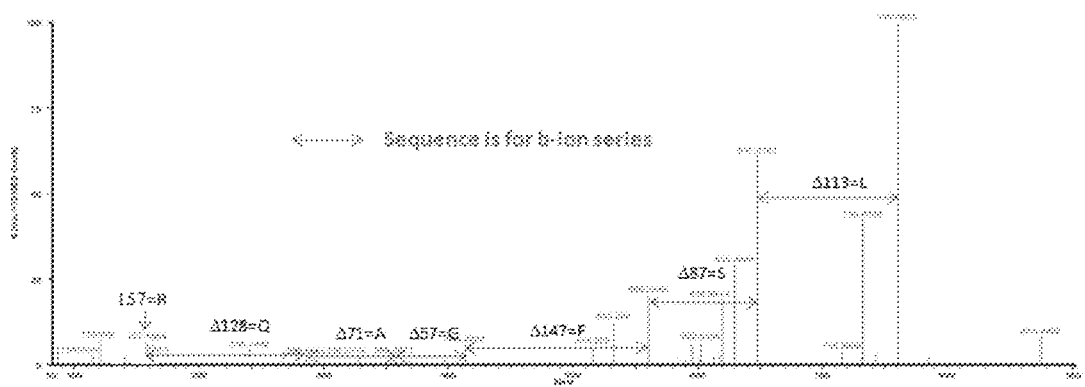
FIGS. 7A and 7B show the detection of fragment ions.
Figure 7B:

The 5-ALA prodrug was designed to release free 5-ALA upon selective Cath E cleavage of the scissile bond between Leu- and 5-ALA residues (FIG. 6A). The biochemical selectivity of the 5-ALA prodrug was systematically tested using a panel of purified proteolytic enzymes, i.e., Cath E, Cath D, and Cath B (50 pmol each). The LC-MS results indicated that Cath E was the only tested protease capable of cleaving the 5-ALA prodrug to two major metabolic fragments, corresponding to H-Arg1-Gln2-Ala3-Gly4-Phe5-Ser6-Leu7-OH and released free 5-ALA8 (FIG. 6B). A higher concentration of Cath B and D (100 pmol) showed no sign of cleavage of the 5-ALA prodrug at the link between 5-ALA and the rest of the peptide substrate, according to LC-MS analysis (data not shown). High energy MS/MS confirmed the production of the metabolic fragments characteristic of selective Cath E-mediated degradation of the 5-ALA prodrug (FIGS. 7A and 7B).

Cath E is a Potent Activator of Drug Release in Cath E-Expressing Cells.

Figure 1B:
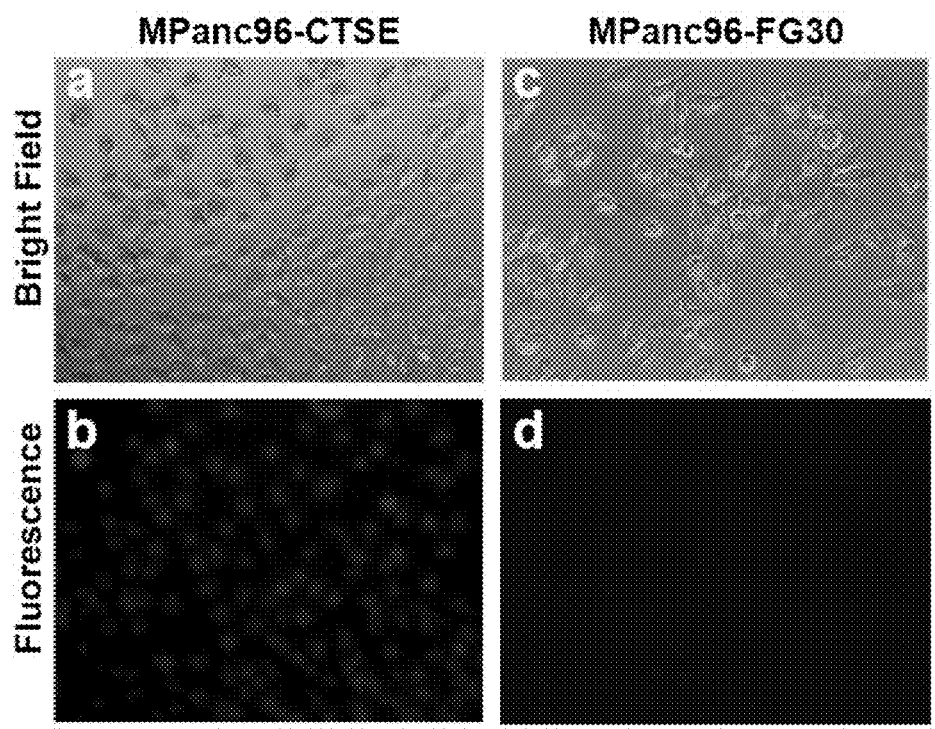

It was shown previously that Cath E expression is upregulated in all stages of PDAC20, including PanIN lesions of human tumor samples and engineered animal models. To explore the potential use of Cath E as a drug activator, the release of model drug 5-ALA was imaged in cells. Although free 5-ALA is not fluorescent, it is the key component for spontaneous synthesis of the fluorescent PpIX molecule. Therefore, Cath E-positive cells, MPanc96-CTSE, were incubated with the 5-ALA prodrug, or free-5-ALA as a positive control, and imaged. Microscopic images of the unfixed MPanc96-CTSE cells in the TRITC channel showed significant PpIX fluorescence signal originating from cells treated with the 5-ALA prodrug (FIG. 1A, panel b). These signals were comparable to those obtained from cells treated with the positive control, free 5-ALA (FIG. 1A, panel d). To further confirm the Cath E-mediated pathway, the 5-ALA prodrug was tested with PDAC cells with a different level of Cath E expression. Pronounced fluorescent signals were observed within PDAC cells with high levels of Cath E enzyme, indicating efficient Cath E-mediated release of 5-ALA (FIG. 1B, panel b). In contrast, PDAC cells of the parent cell line, MPan96-FG30, with limited Cath E expression, failed to show comparable fluorescent signals within the cells, which strongly suggested the lack of free 5-ALA within the cells (FIG. 1B, panel d). This result indicates that Cath E is required to release free 5-ALA and initiate the subsequent synthesis of PpIX.

The 5-ALA Prodrug, in Combination with Light, is an Effective Phototoxic Agent that Selectively Induces PDAC Cell Death In Vitro.

Figure 2:
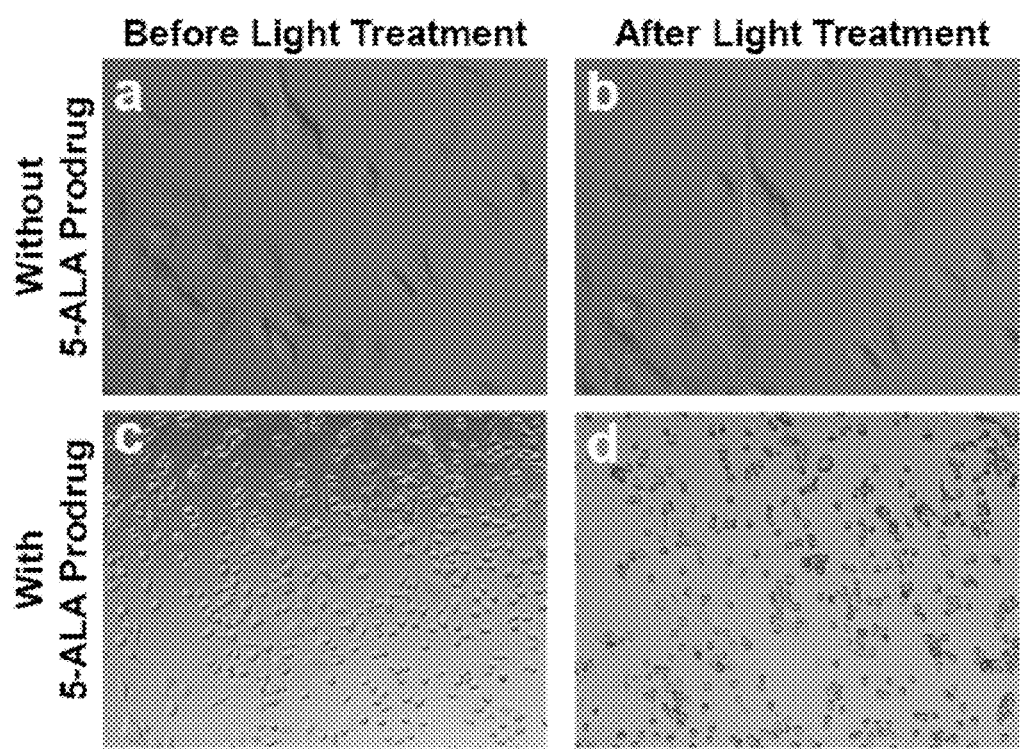
FIG. 2 are photomicrographs showing the 5-ALA prodrug, in combination with light treatment, is an effective phototoxic agent that selectively and sensitively induces cell death in vitro. The microscopic images show unfixed human pancreatic cancer cells (MPanc96-CTSE) untreated (top) and treated with 0.1 µM 5-ALA prodrug (bottom), before (panels a, c) and after (panels b, d) illumination with doses of 18 J/cm2 (top) and 10 J/cm2 (bottom). The cells show no sign of morphological changes upon exposure to high doses of light alone. However, massive cell destruction is observed upon treatment with the 5-ALA prodrug and exposure to a low dose of light.

The potential usefulness of the 5-ALA prodrug was then examined, in combination with light treatment, as a therapeutic agent for PDAC. Cath E-rich cells, MPanc96-CTSE, were treated with the 5-ALA prodrug for 30 minutes, washed, imaged and illuminated. After light treatment, cells were imaged again to assess the effect of the photodynamic treatment. The cells images show no signs of morphological change upon incubation with 5-ALA prodrug without light treatment (FIG. 2, panel c). Similarly, in the absence of the 5-ALA prodrug, the images of cells with or without light illumination showed no change in morphology, even with a high irradiation dose of 90 mW/cm$^2$ (FIG. 2, panels a, b). On the other hand, 5-ALA prodrug-treated cells underwent significant cell death upon treatment with light (FIG. 2, panel d). The images indicate that 5-ALA prodrug alone does not have any apparent cellular toxicity, whereas, upon light treatment, massive damage to the cells was observed. Most cells were greatly altered or destroyed. The light treatment imposed its phototoxic effect only in the event of intracellular release of 5-ALA from the 5-ALA prodrug by Cath E enzyme cleavage.

Figure 3A:
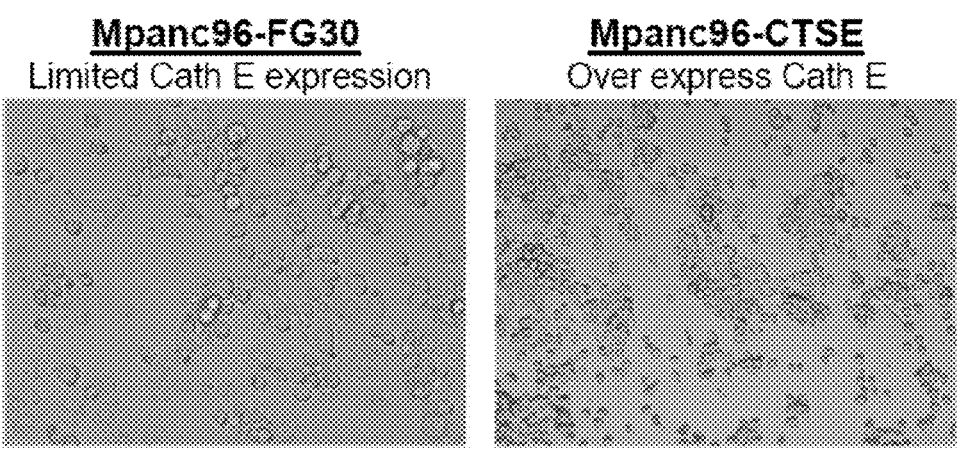
FIGS. 3A-3C show 5-ALA prodrug is an effective phototoxic agent in cells in the presence of light.

To further verify the results, light was applied to the 5-ALA prodrug-treated cells with a different level of Cath E. The images display greater damage to the PDAC cells over-expressing Cath E, MPanc96-CTSE cells (FIG. 3A, right), compared to those having limited Cath E expression, MPanc96-FG30, (FIG. 3A, left). As supported by the fluorescence images (FIG. 1B), the extent of cell damage corresponded to the level of Cath E expression in both cell lines. These results reflect the role of Cath E expression in cleaving the 5-ALA prodrug sequence, resulting in controlled release of 5-ALA and subsequent PpIX synthesis within the tumor cells, which causes cell damage upon light treatment.

Figure 3B:
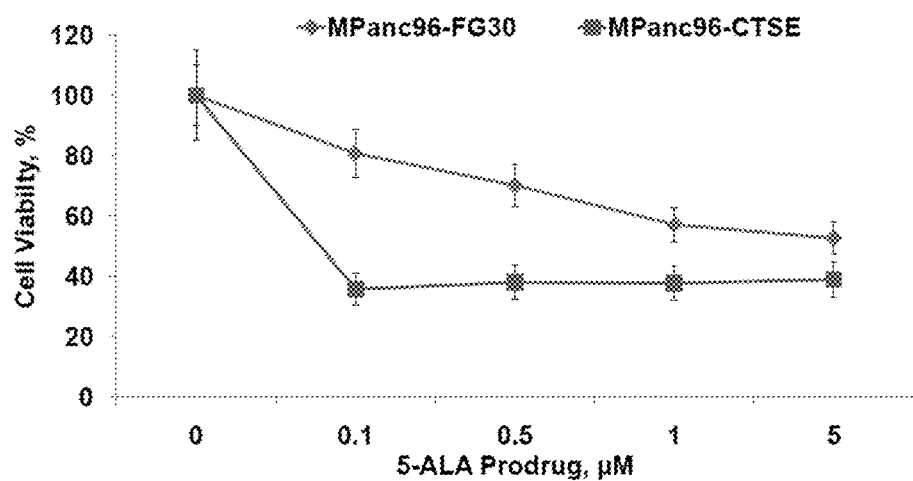
Figure 3C:
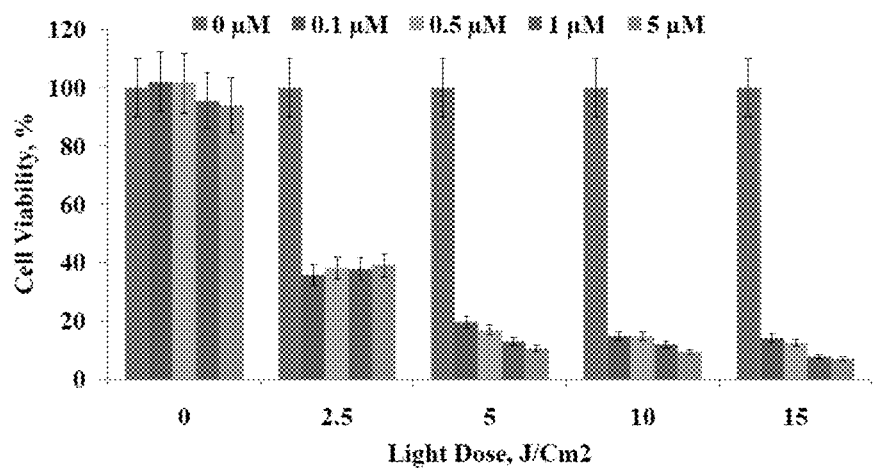

To quantitate cell viability upon photodynamic treatment with the 5-ALA prodrug, PDAC cells were subjected to homogeneous, colorimetric MTS cytotoxicity assay. In this assay, the conversion of MTS into the aqueous soluble formazan product is accomplished only in metabolically active cells. After incubating PDAC cells with the tetrazolium compound, living PDAC cells in culture were quantified directly by measuring the absorbance of the produced formazan product at 490 nm. The cytotoxicity assay results show a rapid decrease in MPanc96-CTSE cell viability, to approximately 40% of the original value, upon PDT using 0.1 µM 5-ALA prodrug and a dose of 2.5 J/cm$^2$ light (FIG. 3B). Meanwhile, a slow and steady decrease in cell viability was observed in MPanc96-FG30, which have limited Cath E expression, upon PDT under the same conditions (FIG. 3B). Increasing the light dose from 2.5 to 5 J/cm$^2$ resulted in a decrease in MPanc96-CTSE cell viability from approximately 40% to approximately 20% (FIG. 3C). Higher light doses (10 and 15 J/cm$^2$) showed no appreciable enhancement of cellular toxicity.

Figure 4:
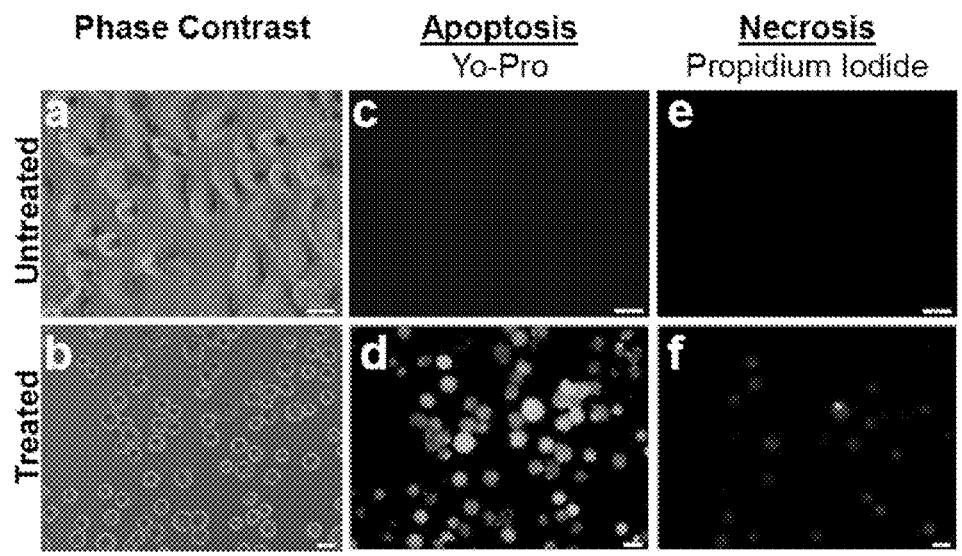
FIG. 4 are photomicrographs (panels a-f) showing the mechanism of 5-ALA prodrug-induced cell death. Representative microscopic images of untreated (top, panels a, c, e) and treated (bottom, panels b, d, f) MPanc96-CTSE cells illustrate apoptotic and necrotic cell damage that occurred during PDT. The images indicate that apoptosis is the primary mechanism of cell death. Cells were stained with both Yo-Pro (apoptosis) and PI (necrosis) immediately after PDT.

The possible pathways of PDAC cell damage were studied by staining the cells using membrane permeability and dead cell apoptosis kit. The PDAC cells were stained with YO-PRO-1 and PI after PDT with the 5-ALA prodrug. Untreated cells were stained as well, for comparison. Images of the PDAC cells after PDT with 5-ALA prodrug showed that the apoptotic cells stained with green fluorescence while dead cells stained with red and green fluorescence (FIG. 4, panels d, f). The apoptotic populations were easily distinguished from the necrotic ones. In contrast, images of cells incubated with the 5-ALA prodrug without light treatment failed to show appreciable YO-PRO-1 and PI fluorescence signals (FIG. 4, panels c, e). The results show that apoptosis is the main pathway of the Cath E-mediated cellular damage imparted by PDT with 5-ALA prodrug.

Photodynamic Therapy with 5-ALA Prodrug Causes Selective PDAC Cell Death In Vivo.

Figure 5:
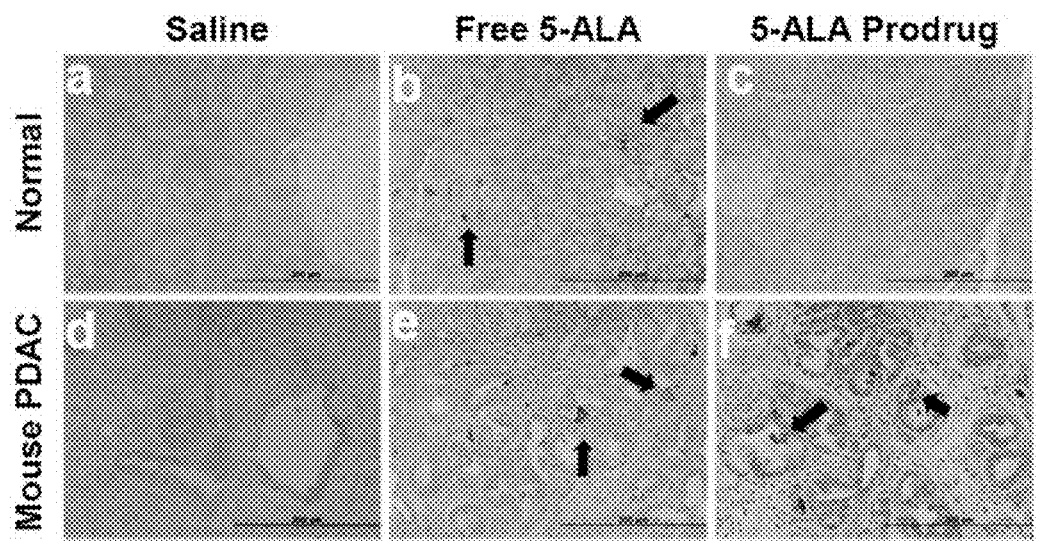
FIG. 5 shows that 5-ALA prodrug in combination with light treatment caused selective pancreatic cancer cell death in vivo. Panels a-c are photomicrographs showing normal pancreas sections and panels d-f show sections of mouse PDAC from a genetic mouse model (p53 conditional deletion/LSL-KrasG12D/Pdx1-Cre) treated with 10 J/cm2. Panels a and d show negative control (saline), panels b and e show positive controls (free 5-ALA), and panels c and f show 5-ALA prodrug treated (1 mg 5-ALA equivalent/kg) samples. Formalin-fixed, paraffin-embedded tissue sections were examined for apoptosis by TUNEL using ApopTag Peroxidase Kit. TUNEL staining of PDAC pancreas sections showed no apoptotic cells in mice treated with saline and PDT (panel d). However, multiple brown-stained cancer cells were observed in pancreas of animals treated with free 5-ALA and 5-ALA prodrug, indicating apoptosis (panels e and f, arrows). Tissue sections of normal pancreas of mice treated with PDT using 5-ALA prodrug showed no apoptotic staining, 5-ALA prodrug sections were similar to the negative saline control (panels a, c). In contrast, scattered brown-stained spots were observed in normal acinar cells in the tissue sections of normal pancreas from mice treated with PDT using free 5-ALA (panel b, arrows).

To examine the selectivity and efficiency of Cath E activation in vivo, the 5-ALA prodrug was tested in genetically engineered mouse models (GEMM). One group of mice with normal pancreases and a second group of mice with PDAC were injected intravenously with saline, free 5-ALA, or 5-ALA prodrug. One hour after IV injection, the abdomen was surgically opened and the exposed pancreases were illuminated locally by a laser. The opening was closed with stitches and the animals allowed to recover for 24 hours. Tissue sections of normal pancreas and PDAC were stained with TUNEL to identify apoptotic cell damage. Tissue sections from mice injected with saline showed no sign of brown staining, indicating that the procedure caused insignificant cell damage (FIG. 5, panels a, d). Similarly, tissue sections from normal mice treated with the 5-ALA prodrug showed no signs of brown staining, reflecting the lack of apoptosis in these tissues (FIG. 5, panel c and Supplementary FIG. 3, right). In contrast, multiple brown-stained spots (highlighted with black arrows) were observed in the tissue sections of normal pancreas from mice treated with free 5-ALA (FIG. 5, panel b and Supplementary FIG. 3, left). Furthermore, multiple apoptotic cells (brown-stained spots) were found in tissue sections from all mice with PDAC treated with free 5-ALA or the 5-ALA prodrug (FIG. 5, panels e, f). This result revealed that free 5-ALA was nonspecifically picked up by normal pancreatic cells and pancreatic cancer cells, and utilized for PpIX synthesis.

Figure 8:
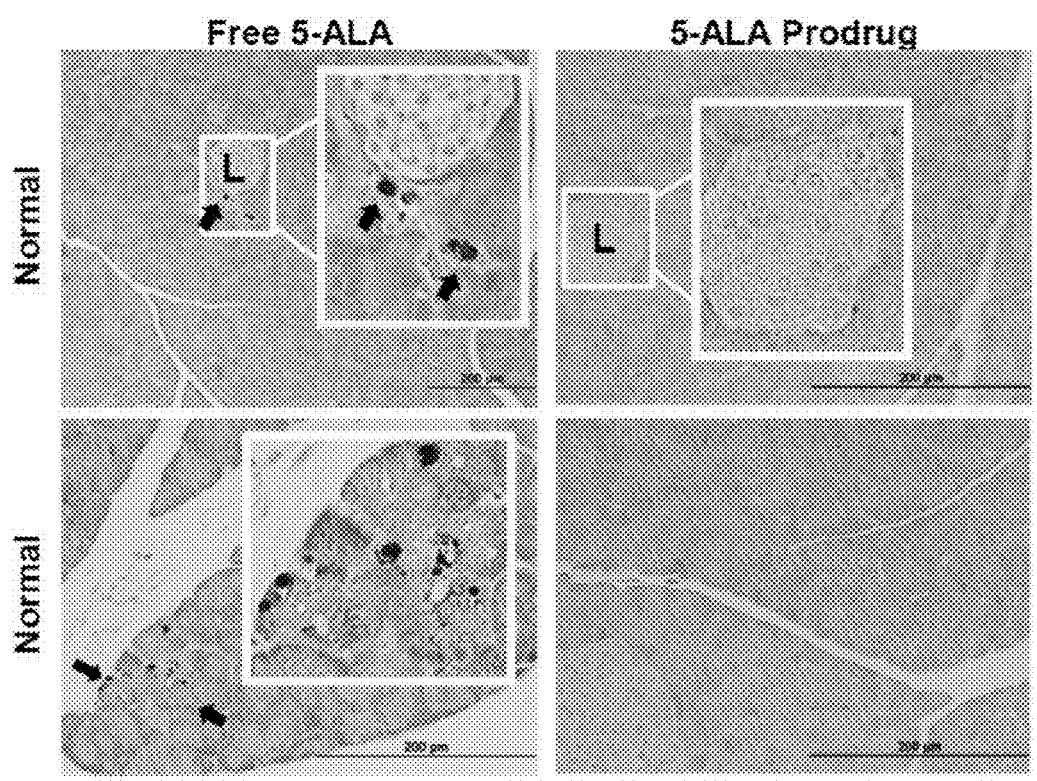
FIG. 8 are photomicrographs of normal pancreas sections from animals treated with free 5-ALA in combination with light treatment to cause nonspecific damage to normal pancreatic cells in vivo. Multiple brown-stained spots in the vicinity of islets of Langerhans (L) (top, left), and in normal acinar cells (bottom, left), were observed in sections of normal pancreas of mice treated with PDT using free 5-ALA, indicating apoptosis in these tissues. In contrast, sections of normal pancreas of mice treated with PDT using 5-ALA prodrug showed no signs of nonspecific apoptosis.

Therefore, light-induced apoptosis was seen in all 5-ALA-treated tissues. Detailed pathological examination of 5-ALA-treated tissues showed non-specific cell damage in areas adjacent to the islets of Langerhans as well as in normal acinar cells (FIG. 8). However, the results with the 5-ALA prodrug were completely different. Because 5-ALA can only be released from the 5-ALA prodrug in Cath E-expressing PDAC and not in normal pancreas, non-specific damage to normal pancreatic tissues were not seen in tissues treated with the 5-ALA prodrug. Therefore, Cath E does play a pivotal role in specific activation of prodrugs design to be activated by this enzyme.

The unique expression of Cath E and its proteolytic activity in neoplastic cells has drawn great attention to its potential use as a biomarker for PDAC. Recently, it was demonstrated that elevated levels of Cath E expression in pancreatic cancer could be exploited for PDAC detection using a novel fluorescent imaging probe (Cruz-Monserrate et al., Gut 61:1315-22 (2012); Abd-Elgaliel, et al., Mol. Biosyst. 7:3207-13 (2011)). To expand the utilization of the distinctive expression of Cath E beyond imaging to specifically kill pancreatic cancer cells, a Cath E-mediated prodrug concept was demonstrated. The prodrug model consists of a 5-ALA residue and a Cath E-sensitive peptide sequence. 5-ALA is the key precursor for hemoglobin. In cells, 5-ALA is utilized spontaneously to synthesize a fluorescent intermediate, PpIX, and then the subsequent chelation of iron forms the final non-fluorescent product, hemoglobin (Kennedy et al., J. Photochem. Photobiol. B 6:143-8 (1990)). 5-ALA by itself is not toxic or fluorescent, but the formed intermediate PpIX is fluorescent and phototoxic. Therefore, in its intact state, the 5-ALA prodrug is insensitive to light illumination and not imageable. Upon selective proteolytic cleavage by the endogenous Cath E, the 5-ALA residue was released and then used to produce PpIX, resulting in a marked PpIX fluorescent signal originating within the neoplastic cells expressing Cath E. This fluorescent signal enabled visualization of the Cath E-expressing tumor cells (FIG. 1A, panel b and FIG. 1B, panel b). In addition, when light illumination at the appropriate wavelength is applied, phototoxicity specific to PDAC cells expressing Cath E is observed and its efficiency is dependent on Cath E expression level (FIG. 2, panel d and FIGS. 3A and 3B). Moreover, promising in vivo PDT effects on Cath E-expressing PDAC cells in GEMM have been shown with a small amount of 5-ALA prodrug (1 mg 5-ALA equivalent/kg) and low light dose (10 J/cm2) (FIG. 5, panel f). Most importantly, selective, targeted cell death of PDAC cells expressing Cath E, but not of normal pancreatic cells, was demonstrated (FIG. 5, panel c). As expected, unmodified 5-ALA photosensitizer caused noticeable nonspecific damage to normal pancreatic tissue, such as normal acinar cells (FIG. 5, panel b) and pancreatic tissue in close proximity to the islets of Langerhans (FIG. 8, top, left). The study described herein is the first demonstration of targeted therapy of pancreatic cancer in GEMM using a novel prodrug specific for Cath E endogenous activity that detects and treats PDAC tumors with minimal damage to the adjacent normal pancreatic tissue.

To improve PDT efficacy, efforts have been focused on ways to escalate cellular damage by improving the spectroscopic and photochemical properties of the photosensitizers, together with use of a state-of-the-art laser beam (van Geel, et al., Br. J. Cancer 72:344-50 (1995); Hopper, Lancet Oncol. 1:212-9(2000)). Pairing of macromolecular moieties, such as polymers and antibodies and, more recently, nanoparticles, is the traditional approach to achieve preferential localization in neoplastic tissues (Choi et al., Chem Med Chem 1:458-63 (2005); Peterson et al., Adv. Exp. Med. Biol. 519:101-23 (2003); Brokx et al., J. Control Release 78:115-23 (2002); Konan et al., J. Photochem. Photobiol. B 66:89-106 (2002); and Jang et al., ACS nano 5:1086-94 (2011)). However, problems, such as early and general sensitization, low selectivity, undesirable phototoxicity to normal cells, and the inconvenience of sustained photosensitivity remained unaddressed until the presently described composition and methods. Investigation of the relative selectivity of the photosensitizer, photofrin, in tumor and normal tissues reveals the lack of an absolute difference in the two types of tissue, which certainly narrows the window of therapeutic application (Hahn et al., Clin. Cancer Res. 12:5464-70 (2006)). Improving the targeting efficiency and avoiding the universal sensitization was need to prevail over limitations of PDT in clinical applications. Previously, the potential use of protease activity in achieving selective imaging was validated (Choi et al., Chem Med Chem 1:698-701 (2006); and Choi et al., Cancer Res. 66:7225-9 (2006)). In the present description, the photosensitizing moiety 5-ALA was modified through conjugation with a peptide sequence that is specifically sensitive to the endogenous proteolytic activity of Cath E in PDAC cells. Since the 5-ALA prodrug in its intact state is insensitive to light illumination, most side effects typically associated with PDT have been largely avoided, including the universal sensitization that caused unwanted phototoxicity to normal cells. Upon intracellular Cath E proteolytic cleavage, the 5-ALA prodrug showed the distinct capacity to localize the PDAC cancer cells and emit fluorescent signals originating within the neoplastic cells. Such a PDAC-specific fluorescent signal could be used to guide surgical procedures. Combined with light illumination, 5-ALA prodrug specifically damages the cancer cells, while minimizing harm to the adjacent normal cells.

This enzyme-activation approach enables selective detection and treatment of pancreatic cancer while sparing normal pancreatic cells. The results of this study described herein provide evidence that Cath E-mediated therapy using the 5-ALA prodrug in combination with light illumination is useful for management of pancreatic cancer. Specifically, the 5-ALA prodrug effectively targeted and killed cancer cells that express Cath E, but not the contiguous normal pancreatic cells in GEMM that mimic human PDAC. Because this approach specifically killed only cancer cells but not normal cells, it will result in fewer side effects than currently available treatments. The use of the PDT approach with the newly developed 5-ALA prodrug will improve survival as it will be able to detect and treat PDAC simultaneously in the same setting or even during surgical procedures.

What is claimed is:

1. A composition comprising a photosensitizer linked to a cleavable substrate, wherein the cleavable substrate is capable of being cleaved by cathepsin E and wherein the cleavable substrate consists of Arg-Gln-Ala-Gly-Phe-Ser-Leu (SEQ ID NO: 1), Gln-Ala-Gly-Phe-Ser-Leu (SEQ ID NO:2), Ala-Gly-Phe-Ser-Leu (SEQ ID NO:3), Gly-Phe-Ser-Leu (SEQ ID NO:4), Phe-Ser-Leu (SEQ ID NO:5), Ser-Leu (SEQ ID NO:6), Arg-Gln-Ala-Gly-Phe-Ser-Phe (SEQ ID NO:7), Gln-Ala-Gly-Phe-Ser-Phe (SEQ ID NO:8), Ala-Gly-Phe-Ser-Phe (SEQ ID NO:9), Gly-Phe-Ser-Phe (SEQ ID NO: 10), Phe-Ser-Phe (SEQ ID NO: 11), Ser-Phe (SEQ ID NO: 12), Ala-Gln-Ala-Gly-Phe-Ser-Leu-Pro-Ala (SEQ ID NO: 13), Gln-Ala-Gly-Phe-Ser-Leu-Pro-Ala (SEQ ID NO: 14), Ala-Gly-Phe-Ser-Leu-Pro-Ala (SEQ ID NO: 15), Gly-Phe-Ser-Leu-Pro-Ala (SEQ ID NO: 16), Phe-Ser-Leu-Pro-Ala (SEQ ID NO: 17), Ser-Leu-Pro-Ala (SEQ ID NO: 18), or Ser-Leu-Pro (SEQ ID NO: 19).

2. The composition of claim 1, wherein the photosensitizer is a porphyrin or a chlorin.

3. The composition of claim 1, wherein the photosensitizer is selected from the group consisting of 5-aminolevulini acid (5-ALA), Rose Bengal, bacteriochlorin, hematoporphyrin, chlorin e6, tetraphenylporphyrin, benzoporphyrin, verteporfin, and porfimer sodium.

4. A composition comprising a chemotherapeutic agent linked to a cleavable substrate, wherein the cleavable substrate is capable of being cleaved by cathepsin E and wherein the cleavable substrate consists of Arg-Gln-Ala-Gly-Phe-Ser-Leu (SEQ ID NO: 1), Gln-Ala-Gly-Phe-Ser-Leu (SEQ ID NO:2), Ala-Gly-Phe-Ser-Leu (SEQ ID NO:3), Gly-Phe-Ser-Leu (SEQ ID NO:4), Phe-Ser-Leu (SEQ ID NO:5), Arg-Gln-Ala-Gly-Phe-Ser-Phe (SEQ ID NO:7), Gln-Ala-Gly-Phe-Ser-Phe (SEQ ID NO:8), Ala-Gly-Phe-Ser-Phe (SEQ ID NO:9), Gly-Phe-Ser-Phe (SEQ ID NO: 10), Phe-Ser-Phe (SEQ ID NO: 11), Ala-Gln-Ala-Gly-Phe-Ser-Leu-Pro-Ala (SEQ ID NO: 13), Gln-Ala-Gly-Phe-Ser-Leu-Pro-Ala (SEQ ID NO: 14), Ala-Gly-Phe-Ser-Leu-Pro-Ala (SEQ ID NO: 15), Gly-Phe-Ser-Leu-Pro-Ala (SEQ ID NO: 16), Phe-Ser-Leu-Pro-Ala (SEQ ID NO: 17), Ser-Leu-Pro-Ala (SEQ ID NO: 18), or Ser-Leu-Pro (SEQ ID NO: 19).

5. The composition of claim 4, wherein the chemotherapeutic agent is selected from the group consisting of gemcitabine, fluorouracil, erlotinib hydrochloride, mitomycin C, doxorubicin, irinotecan, cytoxan, eloxatin, prednisone, vinorelbine, carboplatin, and taxotere.

6. The composition of claim 1, further comprising a pharmaceutically acceptable excipient.

7. A method of treating cancer or pre-cancerous cells characterized by expression of cathepsin E in a subject comprising the steps of: (a) selecting a subject with a disease or disorder characterized by expression of cathepsin E; and
(b) administering to the subject an effective amount of a photosensitizer linked to a cleavable substrate, wherein the cleavable substrate is capable of being cleaved by cathepsin E and wherein the cleavable substrate consists of Arg-Gln-Ala-Gly-Phe-Ser-Leu (SEQ ID NO: 1), Gln-Ala-Gly-Phe-Ser-Leu (SEQ ID NO:2), Ala-Gly-Phe-Ser-Leu (SEQ ID NO:3), Gly-Phe-Ser-Leu (SEQ ID NO:4), Phe-Ser-Leu (SEQ ID NO:5), Ser-Leu (SEQ ID NO:6), Arg-Gln-Ala-Gly-Phe-Ser-Phe (SEQ ID NO:7), Gln-Ala-Gly-Phe-Ser-Phe (SEQ ID NO:8), Ala-Gly-Phe-Ser-Phe (SEQ ID NO:9), Gly-Phe-Ser-Phe (SEQ ID NO: 10), Phe-Ser-Phe (SEQ ID NO: 11), Ser-Phe (SEQ ID NO: 12), Ala-Gln-Ala-Gly-Phe-Ser-Leu-Pro-Ala (SEQ ID NO: 13), Gln-Ala-Gly-Phe-Ser-Leu-Pro-Ala (SEQ ID NO: 14), Ala-Gly-Phe-Ser-Leu-Pro-Ala (SEQ ID NO: 15), Gly-Phe-Ser-Leu-Pro-Ala (SEQ ID NO: 16), Phe-Ser-Leu-Pro-Ala (SEQ ID NO: 17), Ser-Leu-Pro-Ala (SEQ ID NO: 18), or Ser-Leu-Pro (SEQ ID NO: 19).

8. The method of claim 7, wherein the cleavable substrate is cleaved by cathepsin E to separate the cleavable substrate and the photosensitizer.

9. The method of claim 7, further comprising exposing the subject to a light source having a wavelength suitable to activate the photosensitizer.

10. The method of claim 9, wherein the step of exposing the subject to a light source comprises exposing cells in the subject associated with the disease or disorder to a light source having a wavelength suitable to activate the photosensitizer.

11. The method of claim 9, wherein the light source comprises a light-emitting diode or a diode laser.

12. The method of claim 9, wherein the subject or cell is exposed to 1 to 50 $J/Cm^2$ of light.

13. The method of claim 9, wherein activation of the photosensitizer results in death of cells associated with the disease or disorder.

14. The method of claim 7, wherein the cancer is pancreatic cancer, cervical cancer, gastric cancer, prostate cancer, colorectal cancer, breast cancer, adenoendocrine cancer, and lung cancer.

15. The method of claim 14, wherein the pancreatic cancer is pancreactic ductal adenocarcinoma.

16. The method of claim 7, further comprising administering to the subject an additional therapeutic agent suitable for treating one or more symptoms of the disease or disorder characterized by expression of cathepsin E.

17. The method of claim 16, wherein the additional therapeutic agent is a chemotherapeutic agent.

18. The method of claim 7, wherein the photosensitizer is a porphyrin or a chlorin.

19. The method of claim 7, wherein the photosensitizer is selected from the group consisting of 5-aminolevulini acid (5-ALA), Rose Bengal, bacteriochlorin, hematoporphyrin, chlorin e6, tetraphenylporphyrin, benzoporphyrin, verteporfin, and porfimer sodium.

20. A method of treating cancer or pre-cancerous cells symptoms of a disease or disorder characterized by expression of cathepsin E in a subject comprising the steps of: (a) selecting a subject with a disease or disorder characterized by expression of cathepsin E; and
(b) administering to the subject an effective amount of a chemotherapeutic agent linked to a cleavable substrate, wherein the cleavable substrate is capable of being cleaved by cathepsin E and wherein the cleavable substrate consists of Arg-Gln-Ala-Gly-Phe-Ser-Leu (SEQ ID NO: 1), Gln-Ala-Gly-Phe-Ser-Leu (SEQ ID NO:2), Ala-Gly-Phe-Ser-Leu (SEQ ID NO:3), Gly-Phe-Ser-Leu (SEQ ID NO:4), Phe-Ser-Leu (SEQ ID NO:5), Arg-Gln-Ala-Gly-Phe-Ser-Phe (SEQ ID NO:7), Gln-Ala-Gly-Phe-Ser-Phe (SEQ ID NO:8), Ala-Gly-Phe-Ser-Phe (SEQ ID NO:9), Gly-Phe-Ser-Phe (SEQ ID NO: 10), Phe-Ser-Phe (SEQ ID NO: 11), Ala-Gln-Ala-Gly-Phe-Ser-Leu-Pro-Ala (SEQ ID NO: 13), Gln-Ala-Gly-Phe-Ser-Leu-Pro-Ala (SEQ ID NO: 14), Ala-Gly-Phe-Ser-Leu-Pro-Ala (SEQ ID NO: 15), Gly-Phe-Ser-Leu-Pro-Ala (SEQ ID NO: 16), Phe-Ser-Leu-Pro-Ala (SEQ ID NO: 17), Ser-Leu-Pro-Ala (SEQ ID NO: 18), or Ser-Leu-Pro (SEQ ID NO: 19).

21. The method of claim 20, wherein the cleavable substrate is cleaved by cathepsin E to separate the cleavable substrate and the chemotherapeutic agent.

22. The method of claim 20, wherein the chemotherapeutic agent is selected from the group consisting of gemcitabine, fluorouracil, erlotinib hydrochloride, mitomycin C, doxorubicin, irinotecan, cytoxan, eloxatin, prednisone, vinorelbine, carboplatin, and taxotere.

23. The method of claim 20, wherein the cancer is pancreatic cancer, cervical cancer, gastric cancer, prostate cancer, colorectal cancer, breast cancer, adenoendocrine cancer, and lung cancer.

24. The method of claim 23, wherein the pancreatic cancer is pancreactic ductal adenocarcinoma.

25. A method of detecting the presence of a cancer cell expressing cathepsin E comprising the steps of:
  (a) contacting a cell with an effective amount of a photosensitizer linked to a cleavable substrate, wherein the cleavable substrate is capable of being cleaved by cathepsin E and wherein the cleavable substrate consists of Arg-Gln-Ala-Gly-Phe-Ser-Leu (SEQ ID NO: 1), Gln-Ala-Gly-Phe-Ser-Leu (SEQ ID NO:2), Ala-Gly-Phe-Ser-Leu (SEQ ID NO:3), Gly-Phe-Ser-Leu (SEQ ID NO:4), Phe-Ser-Leu (SEQ ID NO:5), Ser-Leu (SEQ ID NO:6), Arg-Gln-Ala-Gly-Phe-Ser-Phe (SEQ ID NO:7), Gln-Ala-Gly-Phe-Ser-Phe (SEQ ID NO:8), Ala-Gly-Phe-Ser-Phe (SEQ ID NO:9), Gly-Phe-Ser-Phe (SEQ ID NO: 10), Phe-Ser-Phe (SEQ ID NO: 11), Ser-Phe (SEQ ID NO: 12), Ala-Gln-Ala-Gly-Phe-Ser-Leu-Pro-Ala (SEQ ID NO: 13), Gln-Ala-Gly-Phe-Ser-Leu-Pro-Ala (SEQ ID NO: 14), Ala-Gly-Phe-Ser-Leu-Pro-Ala (SEQ ID NO: 15), Gly-Phe-Ser-Leu-Pro-Ala (SEQ ID NO: 16), Phe-Ser-Leu-Pro-Ala (SEQ ID NO: 17), Ser-Leu-Pro-Ala (SEQ ID NO: 18), or Ser-Leu-Pro (SEQ ID NO: 19);
  (b) exposing the cell to light having a wavelength suitable to activate the photosensitizer; and
  (c) detecting the level of fluorescence of the photosensitizer, an increase in the level of fluorescence of the photosensitizer as compared to a control indicating the cell is a cancer cell.

26. The method of claim 25, wherein the cell are in vitro or in vivo.

27. The method of claim 25, wherein the cancer cell is a pancreatic cancer cell, wherein the cancer is pancreatic cancer, cervical cancer, gastric cancer, prostate cancer, colorectal cancer, breast cancer, adenoendocrine cancer, and lung cancer.

28. The method of claim 25, wherein the photosensitizer is selected from the group consisting of 5-aminolevulini acid (5-ALA), Rose Bengal, bacteriochlorin, hematoporphyrin, chlorin e6, tetraphenylporphyrin, benzoporphyrin, verteporfin, and porfimer sodium.

29. A method of detecting a cathepsin E expressing cell comprising the steps of:
  (a) contacting a cell with an effective amount of a photosensitizer linked to a cleavable substrate, wherein the cleavable substrate is capable of being cleaved by cathepsin E and wherein the cleavable substrate comprises Arg-Gln-Ala-Gly-Phe-Ser-Leu (SEQ ID NO:1), Gln-Ala-Gly-Phe-Ser-Leu (SEQ ID NO:2), Ala-Gly-Phe-Ser-Leu (SEQ ID NO:3), Gly-Phe-Ser-Leu (SEQ ID NO:4), Phe-Ser-Leu (SEQ ID NO:5), Ser-Leu (SEQ ID NO:6), Arg-Gln-Ala-Gly-Phe-Ser-Phe (SEQ ID NO:7), Gln-Ala-Gly-Phe-Ser-Phe (SEQ ID NO:8), Ala-Gly-Phe-Ser-Phe (SEQ ID NO:9), Gly-Phe-Ser-Phe (SEQ ID NO:10), Phe-Ser-Phe (SEQ ID NO:11), Ser-Phe (SEQ ID NO:12), Ala-Gln-Ala-Gly-Phe-Ser-Leu-Pro-Ala (SEQ ID NO:13), Gln-Ala-Gly-Phe-Ser-Leu-Pro-Ala (SEQ ID NO:14), Ala-Gly-Phe-Ser-Leu-Pro-Ala (SEQ ID NO:15), Gly-Phe-Ser-Leu-Pro-Ala (SEQ ID NO:16), Phe-Ser-Leu-Pro-Ala (SEQ ID NO:17), Ser-Leu-Pro-Ala (SEQ ID NO:18), or Ser-Leu-Pro (SEQ ID NO:19);
  (b) exposing the cell to light having a wavelength suitable to activate the photosensitizer; and
  (c) detecting fluorescence of the photosensitizer, fluorescence of the photosensitizer above background indicating the cell is a cathepsin E expressing cell.

30. The method of claim 29, wherein the cell is in vitro or in vivo.

31. The method of claim 29, wherein the photosensitizer is selected from the group consisting of 5-aminolevulini acid (5-ALA), Rose Bengal, bacteriochlorin, hematoporphyrin, chlorin e6, tetraphenylporphyrin, benzoporphyrin, verteporfin, and porfimer sodium.

32. A kit comprising the composition of claim 1 in one or more suitable containers.

33. The kit of claim 32, further comprising an additional therapeutic agent.

34. The kit of claim 33, wherein the therapeutic agent is a chemotherapeutic agent.

35. The kit of claim 32, further comprising instructions for use.

* * * * *

UNITED STATES PATENT AND TRADEMARK OFFICE
CERTIFICATE OF CORRECTION

PATENT NO. : 9,439,976 B2
APPLICATION NO. : 14/179379
DATED : September 13, 2016
INVENTOR(S) : Ching-Hsuan Tung et al.

Page 1 of 1

It is certified that error appears in the above-identified patent and that said Letters Patent is hereby corrected as shown below:

In the Specification

Column 1, Lines 15 and 16:
Replace "This invention was made under government Grant No. R01 CA135312 from the National Institutes of Health. The" with --This invention was made with government support under grant number CA135312 awarded by the National Institutes of Health. The--

Signed and Sealed this
Twenty-eighth Day of April, 2020

Andrei Iancu
*Director of the United States Patent and Trademark Office*

SEQUENCE LISTING

<160> NUMBER OF SEQ ID NOS: 19

<210> SEQ ID NO 1
<211> LENGTH: 7
<212> TYPE: PRT

```
<213> ORGANISM: Artificial Sequence
<220> FEATURE:
<223> OTHER INFORMATION: Cleavable Substrate 1

<400> SEQUENCE: 1

Arg Gln Ala Gly Phe Ser Leu
1               5

<210> SEQ ID NO 2
<211> LENGTH: 6
<212> TYPE: PRT
<213> ORGANISM: Artificial Sequence
<220> FEATURE:
<223> OTHER INFORMATION: Cleavable Substrate 2

<400> SEQUENCE: 2

Gln Ala Gly Phe Ser Leu
1               5

<210> SEQ ID NO 3
<211> LENGTH: 5
<212> TYPE: PRT
<213> ORGANISM: Artificial Sequence
<220> FEATURE:
<223> OTHER INFORMATION: Cleavable Substrate 3

<400> SEQUENCE: 3

Ala Gly Phe Ser Leu
1               5

<210> SEQ ID NO 4
<211> LENGTH: 4
<212> TYPE: PRT
<213> ORGANISM: Artificial Sequence
<220> FEATURE:
<223> OTHER INFORMATION: Cleavable Substrate 4

<400> SEQUENCE: 4

Gly Phe Ser Leu
1

<210> SEQ ID NO 5
<211> LENGTH: 3
<212> TYPE: PRT
<213> ORGANISM: Artificial Sequence
<220> FEATURE:
<223> OTHER INFORMATION: Cleavable Substrate 5

<400> SEQUENCE: 5

Phe Ser Leu
1

<210> SEQ ID NO 6
<211> LENGTH: 2
<212> TYPE: PRT
<213> ORGANISM: Artificial Seqeucne
<220> FEATURE:
<223> OTHER INFORMATION: Cleavable Substrate 6

<400> SEQUENCE: 6

Ser Leu
1

<210> SEQ ID NO 7
<211> LENGTH: 7
<212> TYPE: PRT
<213> ORGANISM: Artificial Sequence
```

```
<220> FEATURE:
<223> OTHER INFORMATION: Cleavable Substrate 7

<400> SEQUENCE: 7

Arg Gln Ala Gly Phe Ser Phe
1               5

<210> SEQ ID NO 8
<211> LENGTH: 6
<212> TYPE: PRT
<213> ORGANISM: Artificial Sequence
<220> FEATURE:
<223> OTHER INFORMATION: Cleavable Substrate 8

<400> SEQUENCE: 8

Gln Ala Gly Phe Ser Phe
1               5

<210> SEQ ID NO 9
<211> LENGTH: 5
<212> TYPE: PRT
<213> ORGANISM: Artificial Sequence
<220> FEATURE:
<223> OTHER INFORMATION: Cleavable Substrate 9

<400> SEQUENCE: 9

Ala Gly Phe Ser Phe
1               5

<210> SEQ ID NO 10
<211> LENGTH: 4
<212> TYPE: PRT
<213> ORGANISM: Artificial Sequence
<220> FEATURE:
<223> OTHER INFORMATION: Cleavable Substrate 10

<400> SEQUENCE: 10

Gly Phe Ser Phe
1

<210> SEQ ID NO 11
<211> LENGTH: 3
<212> TYPE: PRT
<213> ORGANISM: Artificial Sequence
<220> FEATURE:
<223> OTHER INFORMATION: Cleavable Substrate 11

<400> SEQUENCE: 11

Phe Ser Phe
1

<210> SEQ ID NO 12
<211> LENGTH: 2
<212> TYPE: PRT
<213> ORGANISM: Artificial Sequence
<220> FEATURE:
<223> OTHER INFORMATION: Cleavable Substrate 12

<400> SEQUENCE: 12

Ser Phe
1

<210> SEQ ID NO 13
<211> LENGTH: 9
<212> TYPE: PRT
<213> ORGANISM: Artificial Sequence
<220> FEATURE:
```

<223> OTHER INFORMATION: Cleavable Substrate 13

<400> SEQUENCE: 13

Ala Gln Ala Gly Phe Ser Leu Pro Ala
1               5

<210> SEQ ID NO 14
<211> LENGTH: 8
<212> TYPE: PRT
<213> ORGANISM: Artificial Sequence
<220> FEATURE:
<223> OTHER INFORMATION: Cleavable Substrate 14

<400> SEQUENCE: 14

Gln Ala Gly Phe Ser Leu Pro Ala
1               5

<210> SEQ ID NO 15
<211> LENGTH: 7
<212> TYPE: PRT
<213> ORGANISM: Artificial Sequence
<220> FEATURE:
<223> OTHER INFORMATION: Cleavable Substrate 15

<400> SEQUENCE: 15

Ala Gly Phe Ser Leu Pro Ala
1               5

<210> SEQ ID NO 16
<211> LENGTH: 6
<212> TYPE: PRT
<213> ORGANISM: Artificial Sequence
<220> FEATURE:
<223> OTHER INFORMATION: Cleavable Substrate 16

<400> SEQUENCE: 16

Gly Phe Ser Leu Pro Ala
1               5

<210> SEQ ID NO 17
<211> LENGTH: 5
<212> TYPE: PRT
<213> ORGANISM: Artificial Sequence
<220> FEATURE:
<223> OTHER INFORMATION: Cleavable Substrate 17

<400> SEQUENCE: 17

Phe Ser Leu Pro Ala
1               5

<210> SEQ ID NO 18
<211> LENGTH: 4
<212> TYPE: PRT
<213> ORGANISM: Artificial Sequence
<220> FEATURE:
<223> OTHER INFORMATION: Cleavable Substrate 18

<400> SEQUENCE: 18

Ser Leu Pro Ala
1

<210> SEQ ID NO 19
<211> LENGTH: 3
<212> TYPE: PRT
<213> ORGANISM: Artificial Sequence
<220> FEATURE:
<223> OTHER INFORMATION: Cleavable Substrate 19

```
<400> SEQUENCE: 19

Ser Leu Pro
1
```